US012690826B2

(12) United States Patent
DeFreitas et al.

(10) Patent No.: US 12,690,826 B2
(45) Date of Patent: Jul. 28, 2026

(54) PATIENT SHIELD FOR AN X-RAY IMAGING SYSTEM AND METHODS OF THE SAME

(71) Applicant: Hologic, Inc., Marlborough, MA (US)

(72) Inventors: Kenneth F. DeFreitas, Patterson, NY (US); Baorui Ren, Andover, MA (US); Brent L. Burchfield, Powell, OH (US); Zhenxue Jing, Chadds Ford, PA (US)

(73) Assignee: Hologic, Inc., Marlborough, MA (US)

( * ) Notice: Subject to any disclaimer, the term of this patent is extended or adjusted under 35 U.S.C. 154(b) by 318 days.

(21) Appl. No.: 18/551,278

(22) PCT Filed: Mar. 21, 2022

(86) PCT No.: PCT/US2022/021139
§ 371 (c)(1),
(2) Date: Sep. 19, 2023

(87) PCT Pub. No.: WO2022/204024
PCT Pub. Date: Sep. 29, 2022

(65) Prior Publication Data
US 2024/0188908 A1 Jun. 13, 2024

Related U.S. Application Data

(60) Provisional application No. 63/260,029, filed on Aug. 6, 2021, provisional application No. 63/166,820, filed on Mar. 26, 2021.

(51) Int. Cl.
*A61B 6/00* (2024.01)
*A61B 6/02* (2006.01)
(Continued)

(52) U.S. Cl.
CPC .............. *A61B 6/107* (2013.01); *A61B 6/025* (2013.01); *A61B 6/0414* (2013.01); *A61B 6/4435* (2013.01); *A61B 6/502* (2013.01)

(58) Field of Classification Search
CPC ......... A61B 6/502; A61B 90/11; A61B 90/17; A61B 6/04; A61B 6/44; A61B 2017/3409;
(Continued)

(56) References Cited

U.S. PATENT DOCUMENTS

| | | | |
|---|---|---|---|
| 8,787,522 | B2 | 7/2014 | Smith et al. |
| 10,194,875 | B2 | 2/2019 | DeFreitas et al. |

(Continued)

FOREIGN PATENT DOCUMENTS

| | | |
|---|---|---|
| CN | 104323788 A | 2/2015 |
| CN | 105491953 A | 4/2016 |

(Continued)

OTHER PUBLICATIONS

PCT International Search Report and Written Opinion in Application PCT/US2022/021139, mailed Aug. 11, 2022, 23 pages.
(Continued)

*Primary Examiner* — Don K Wong
(74) *Attorney, Agent, or Firm* — Merchant & Gould P.C.

(57) ABSTRACT

An imaging system (100) includes a gantry (126) and a compression arm assembly (104). The compression arm assembly (104) including a support arm (122) supporting a compression paddle (108), a platform (106), and an x-ray receptor (114). An x-ray tube head (124) includes an x-ray source (120). A patient shield system (138) is disposed between the compression paddle (108) and the x-ray source (120). The patient shield system (138) includes an arm (142), a carrier (144), a shield (140), and at least one leg (416, 450, 475, 502) supporting the shield (140) on the carrier (144). A 0° tube head angle is defined as the x-ray source (120) being orthogonal to the support platform (106), and the at least one leg (416, 450, 475, 502) is positioned on the support arm (122) such that the at least one leg (416, 450, 475, 502) is between a ±8° and ±15° tube head angle.

20 Claims, 17 Drawing Sheets

(51) Int. Cl.
  *A61B 6/04*        (2006.01)
  *A61B 6/10*        (2006.01)
  *A61B 6/50*        (2024.01)

(58) Field of Classification Search
  CPC .. A61B 2090/376; A61B 34/25; A61B 6/0414
  See application file for complete search history.

(56)                    References Cited

U.S. PATENT DOCUMENTS

| | | |
|---|---|---|
| 2007/0036265 A1 | 2/2007 | Jing et al. |
| 2009/0323892 A1 | 12/2009 | Hitzke et al. |
| 2016/0270742 A9 | 9/2016 | Stein et al. |
| 2018/0199906 A1 | 7/2018 | Kobayashi et al. |
| 2021/0401381 A1 | 12/2021 | Wells et al. |
| 2022/0133252 A1* | 5/2022 | Smith ................... A61B 6/032 |
| | | 378/4 |

FOREIGN PATENT DOCUMENTS

| | | |
|---|---|---|
| EP | 1759637 | 3/2007 |
| EP | 2679157 | 1/2014 |
| EP | 3381372 | 10/2018 |
| WO | 2010028208 | 3/2010 |

OTHER PUBLICATIONS

PCT International Preliminary Report on Patentability in Application PCT/US2022/021139, mailed Oct. 5, 2023, 18 pages.
Anonymous, "Screening Mammogram Need to Knows—(fairly) comprehensive", UNC Radiology medical student education website, Jan. 1, 2018, XP093314393.
European Communication pursuant to Article 94(3) EPC in U.S. Appl. No. 22/715,854, mailed Sep. 18, 2025, 7 pages.
Chinese 1st Office Action and Search Report in Application 202280024190.3, mailed Apr. 15, 2026, 5 pages.

* cited by examiner

FRAMES #14    #15        #16        #17        #18        #19        #20

FRAMES #36    #37        #38        #39        #40        #41        #42

PATIENT SHIELD FOR AN X-RAY IMAGING SYSTEM AND METHODS OF THE SAME

CROSS-REFERENCE TO RELATED APPLICATIONS

This application is a National Stage Application of PCT/US2022/021139, filed on Mar. 21, 2022, which claims the benefit of U.S. Provisional Application No. 63/260,029, filed Aug. 6, 2021, and U.S. Provisional Application No. 63/166,820, filed Mar. 26, 2021, the entire disclosures of which are incorporated herein by reference in their entireties. To the extent appropriate, a claim of priority is made to each of the above disclosed applications.

BACKGROUND

Compression during x-ray imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technologist manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed in an imaging area on a breast support platform that typically is flat, and the paddle then compresses the breast, usually while a technologist or other health professional is holding the breast in place. The technologist may also manipulate the breast to ensure proper tissue coverage in the image receptor's field of view. Additionally, a patient shield may be positioned by the technologist between the patient and the x-ray field to restrict patient from encroaching into the images.

At least some known patient shields are coupled to the imaging system and are shaped and sized for standard mammography and tomosynthesis imaging. However, some known imaging systems also allow for increased wider angle imaging positions (e.g., a 60° sweep by the tube head), which increases the imaging area for the patient shield to cover. As such, improvements to patient shields are desired.

SUMMARY

In one aspect, the technology relates to an imaging system for imaging a patient's breast including: a gantry; a compression arm assembly rotatably coupled to the gantry, the compression arm assembly including a support arm supporting a compression paddle, a platform, and an x-ray receptor disposed below the platform; an x-ray tube head rotatably coupled to the gantry and independently rotatable relative to the compression arm assembly, the x-ray tube head including an x-ray source that is moveable along a first plane via the x-ray tube head; and a patient shield system disposed at least partially between the compression paddle and the x-ray source, the patient shield system including: an arm removably coupled to the support arm; a carrier slidably coupled to the arm; a shield; and a bracket coupling the shield to the carrier, wherein the bracket includes a shield mount coupled to the shield and a carrier mount coupled to the carrier, the shield mount engaged with the carrier mount to allow the shield to be slidingly moved relative to the carrier, and wherein the bracket defines a path of travel for the shield that is in a second plane parallel to the first plane, the path of travel having an arcuate shape.

In an example, the shield includes a flat plate. In another example, an angular displacement of the shield along the path of travel is at least 60°. In still another example, the carrier mount includes a radiolucent plate secured to the carrier. In yet another example, the carrier mount includes a support configured to engage the shield mount and a pair of legs extending from the support and configured to couple to the carrier, and an opening is defined by the support, the pair of legs, and the carrier, the opening shaped and sized to allow x-rays to pass through the patient shield system.

In another aspect, the technology relates to an imaging system for imaging a patient's breast including: a gantry; a compression arm assembly rotatably coupled to the gantry, the compression arm assembly including a support arm supporting a compression paddle, a platform, and an x-ray receptor disposed below the platform; an x-ray tube head rotatably coupled to the gantry and independently rotatable relative to the compression arm assembly around a rotation axis, the x-ray tube head including an x-ray source that is rotatable along a first plane via the x-ray tube head; and a patient shield system disposed at least partially between the compression paddle and the x-ray source, the patient shield system including: an arm removably coupled to the support arm and defining a longitudinal axis; a carrier slidably coupled to the arm; a shield; and a bracket coupling the shield to the carrier, wherein the bracket is configured to allow the shield to move along a transverse plane orthogonal to the longitudinal axis, and wherein a path of travel for the shield along the transverse plane has an arcuate shape.

In an example, a 0° tube head angle is defined as the x-ray tube head being orthogonal to the platform, and the shield is movable along the path of travel between at least ±30° relative to the 0° tube head angle. In another example, the shield has a first edge and an opposite second edge, and when the shield is moved in a direction towards the first edge, the first edge is positionable past 30°, and when the shield is moved in a direction towards the second edge, the second edge is positionable past −30°. In still another example, the bracket further includes a locking mechanism to secure a position of the shield relative to the carrier. In yet another example, the arcuate shape is defined around the rotational axis.

In another aspect, the technology relates to a method of imaging a patient's breast including: positioning a compression arm assembly, the compression arm assembly including a support arm supporting a compression paddle, a platform, and an x-ray receptor disposed below the platform; immobilizing the patient's breast between the compression paddle and the platform; positioning a shield at least partially between the patient and an x-ray field of an x-ray source of an x-ray tube head, the shield being coupled to the support arm by at least an arm and a carrier, wherein the shield is movable relative to the support arm linearly along the arm via the carrier and transversely along a plane orthogonal to the arm via a bracket, and wherein a path of travel of the shield is arcuate in shape along the transverse plane; acquiring one or more first x-ray images in at least one first imaging mode, wherein the at least one first imaging mode is at tube head angles less than or equal to ±7° relative to a 0° tube head angle; and acquiring one or more second x-ray images in a second imaging mode, wherein the second imaging mode is at tube head angles greater than ±7° relative to the 0° tube head angle, and wherein the shield is positioned relative to the x-ray field of the second imaging mode.

In an example, the method further includes locking a position of the shield relative to the compression arm assembly. In another example, the at least one first imaging mode includes tomosynthesis imaging. In still another example, the at least one first imaging mode includes mammography imaging. In yet another example, the at least one first imaging mode includes tomosynthesis and mammography imaging. In an example, the second imaging mode is mode is enhanced tomosynthesis. In another example, positioning the compression arm assembly includes positioning a compression arm assembly in an MLO imaging position.

In another aspect, the technology relates to an imaging system for imaging a patient's breast including: a gantry; a compression arm assembly rotatably coupled to the gantry, the compression arm assembly including a support arm supporting a compression paddle, a platform, and an x-ray receptor disposed below the platform; an x-ray tube head rotatably coupled to the gantry and independently rotatable relative to the compression arm assembly, the x-ray tube head including an x-ray source; and a patient shield system disposed at least partially between the compression paddle and the x-ray source, the patient shield system including: an arm removably coupled to the support arm; a carrier slidably coupled to the arm; a shield; and at least one leg supporting the shield on the carrier, wherein a 0° tube head angle is defined as the x-ray source being orthogonal to the support platform, and wherein the at least one leg is positioned on the support arm such that the at least one leg is between a ±8° and ±15° tube head angle.

In an example, when the x-ray source is at a ±8° tube head angle, an image artifact of the at least one leg is not generated during imaging. In another example, when the x-ray source is at a ±15° tube head angle, an image artifact of the at least one leg is not generated during imaging. In still another example, a cross-sectional profile of the at least one leg is triangular in shape. In yet another example, a cross-sectional profile of the at least one leg is circular in shape. In an example, a cross-sectional profile of the at least one leg is quadrilateral in shape. In another example, the at least one leg includes a pair of legs.

In another aspect, the technology relates to a method of imaging a patient's breast including: immobilizing the patient's breast in a compression arm assembly including a support arm supporting a compression paddle, a platform, and an x-ray receptor disposed below the platform; positioning a shield at least partially between the patient and an x-ray field of an x-ray tube head, the shield being positioned on one side of a tube head plane with at least one leg supporting the shield and extending across the tube head plane; acquiring a plurality of x-ray projection images of the patient's breast during tomosynthesis imaging, wherein at least two of the plurality of x-ray projection images include an image artifact from the at least one leg, the at least one leg shaped and sized such that a location of the image artifact within the at least two x-ray projection images do not overlap with one another; processing the at least two x-ray projection images; and reconstructing one or more tomosynthesis images based on the processed at least two x-ray projection images.

In an example, acquiring the at least two x-ray projection images includes emitting x-ray exposures between a ±8° and ±15° tube head angle. In another example, processing the at least two x-ray projection images includes identifying a location of the image artifact and segmenting the image artifact with a background value. In still another example, identifying the location of the image artifact includes determining a position of two outermost edges of the image artifact. In yet another example, the method further includes processing an x-ray projection image with a partial image artifact of the at least one leg, wherein based on the determined position of at least one of the two outermost edges, a fitting curve is generated such that an edge of the partial image artifact is determined from the at least two x-ray projection images having two outermost edges. In an example, reconstructing the one or more tomosynthesis images is performed using back-projection in a spatial domain or in a frequency domain.

In another aspect, the technology relates to a method of imaging a patient's breast including: immobilizing the patient's breast in a compression arm assembly including a support arm supporting a compression paddle, a platform, and an x-ray receptor disposed below the platform; positioning a shield at least partially between the patient and an x-ray field of an x-ray tube head, the shield being positioned on one side of a tube head plane with at least one leg supporting the shield and extending across the tube head plane; acquiring a plurality of x-ray projection images of the patient's breast during tomosynthesis imaging, wherein at least one of the plurality of x-ray projection images include an image artifact from the at least one leg; identifying a location of the image artifact in the at least one x-ray projection image; segmenting the image artifact with a background value; and reconstructing one or more tomosynthesis images based on the segmented at least one x-ray projection image.

In an example, acquiring the at least one x-ray projection image includes emitting x-ray exposures between a ±8° and ±15° tube head angle. In another example, the at least one x-ray projection image having the image artifact includes at least two x-ray projection images having the image artifact from the at least one leg, the at least one leg shaped and sized such that a location of the image artifact within the at least two x-ray projection images do not overlap with one another. In still another example, identifying the location of the image artifact includes determining a position of two outermost edges of the image artifact. In yet another example, the method further includes processing an x-ray projection image with a partial image artifact of the at least one leg, wherein based on the determined position of at least one of the two outermost edges, a fitting curve is generated such that an edge of the partial image artifact is determined from the at least two x-ray projection images having two outermost edges.

DETAILED DESCRIPTION

Figure 1:
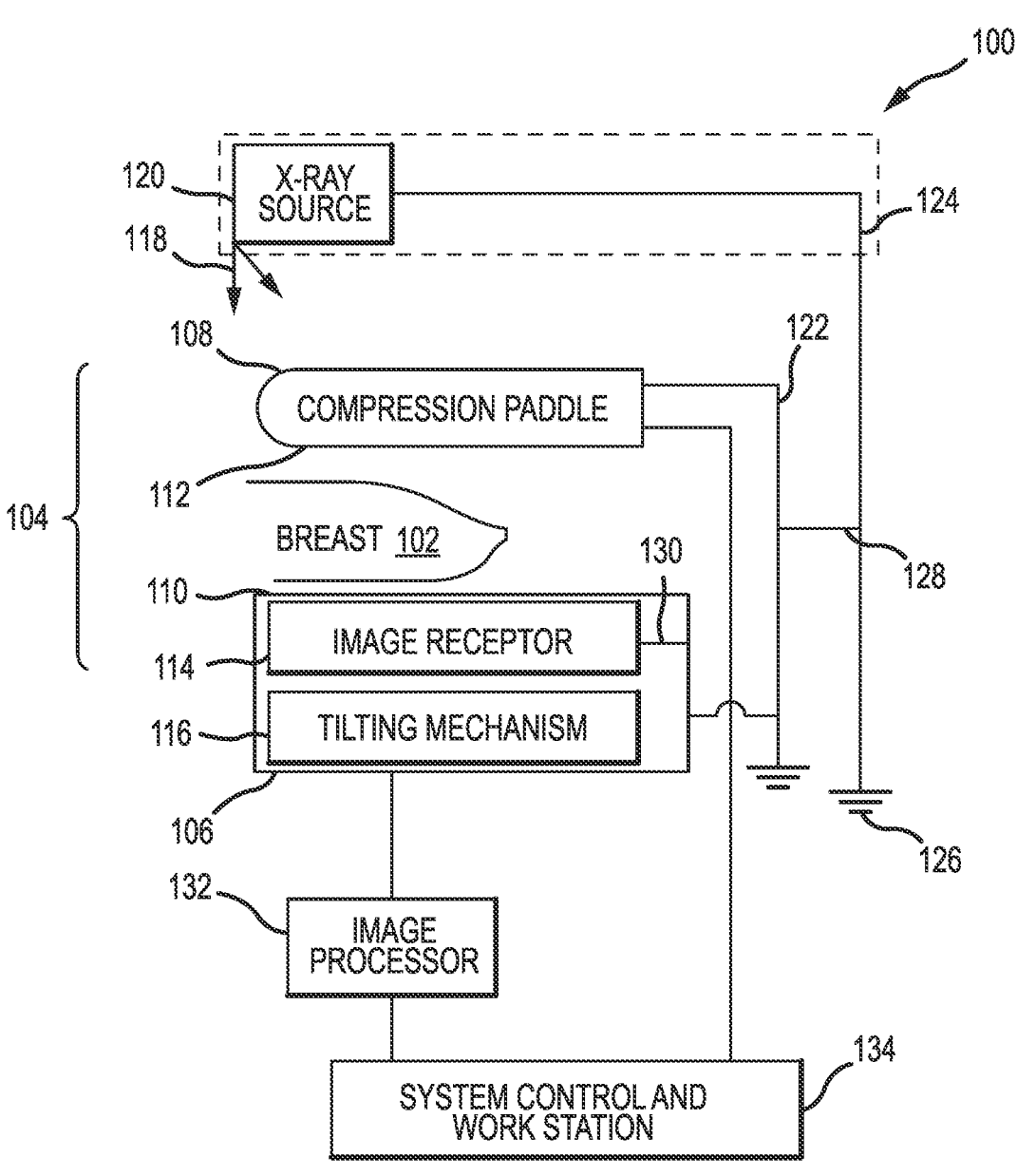
FIG. 1 is a schematic view of an exemplary imaging system.

The technologies described herein relate to a patient shield system having a sliding shield that increases the reach of the shield and accommodates wide angle imaging on an imaging system. By increasing the reach of the shield, patient comfort is increased by restricting contact with the moving x-ray tube head of the imaging system even at wide angle imaging positions, for example, a 60° tube head sweep. The shield can also help with positioning and support of the patient at the imaging system for comfort during immobilization. Additionally, the shield guards against the patient from encroaching into the x-ray field during imaging at the wide angle imaging positions.

One option to support this type of sliding shield is to have a frame that is positioned outside of the imaging area that includes the wide angle image positions of the x-ray tube head. However, using a frame that is outside of the wide angle imaging area results in a large frame that restricts access to the compression arm assembly for the technologist to position the patient's breast. As such, the patient shield system described herein is coupled to the compression arm assembly and can be adjustable for retraction (e.g., forward or backward relative to the front edge of the support platform) so that the shield can be moved and allow technologist access to the support platform and compression paddle. In addition, the shield can slide along a transverse plane relative to the retraction direction so as to position the shield between the patient and the x-ray field even at wide angle image positions.

In the examples described herein, the shield is positioned between the patient and the x-ray field, and as such, a portion of the patient shield system extends through the x-ray imaging area in order to support the position of the shield. The patient shield system includes a bracket that extends through the x-ray imaging area and enables the sliding movement of the shield. In an aspect, at least a portion of the bracket is formed from a radiolucent material that is positioned adjacent to the focal spot of the x-ray source so that image attenuation is reduced. In this example, the x-ray beams are emitted through the bracket for one or more imagine acquisitions. When images are acquired at the sides of the bracket, the image acquisition process may skip over these angular positions, or any image artifacts that may form from the bracket can be reduced or removed by the work station. In another aspect, the bracket may be formed by a pair of spaced apart legs that extend through the x-ray imaging system. As such, an opening is formed to allow x-ray beams to pass through without obstruction. When images are acquired at the leg positions, the image acquisition process may skip over these angular portions, or any image artifacts that may form from the bracket can be reduced or removed by the work station. In an aspect, the image acquisition process may shoot through the leg positions, and the work station is configured to process the projection images so as to provide image artifact correction and improve the resulting reconstruction images.

Accordingly, the patient shield system and sliding shield is configured to reduce or prevent patient contact with moving components during imaging procedures and to increase patient comfort around moving components. Additionally, the shield guards against the patient entering the x-ray field during imaging procedures. However, the patient shield system and shield also provides access for the technologist to position the patient's breast for immobilization. As such, in combo imaging systems, the patient shield system and the sliding shield described herein are configured to be positioned relative to the support platform such that the shield can accommodate not only mammography and tomosynthesis imaging positions, but also wide angle imaging positions, while still enabling access to the compression arm assembly for the technologist to immobilize the patient's breast.

Additionally, the bracket of the patient shield system is robust and is able to support the cantilevered sliding positions of the shield, even when the patient is pressing against the shield and applying a force to the patient shield system. As such, the shield can support the patient in its extended position and without deflecting into the x-ray field of the imaging system.

Figure 2:
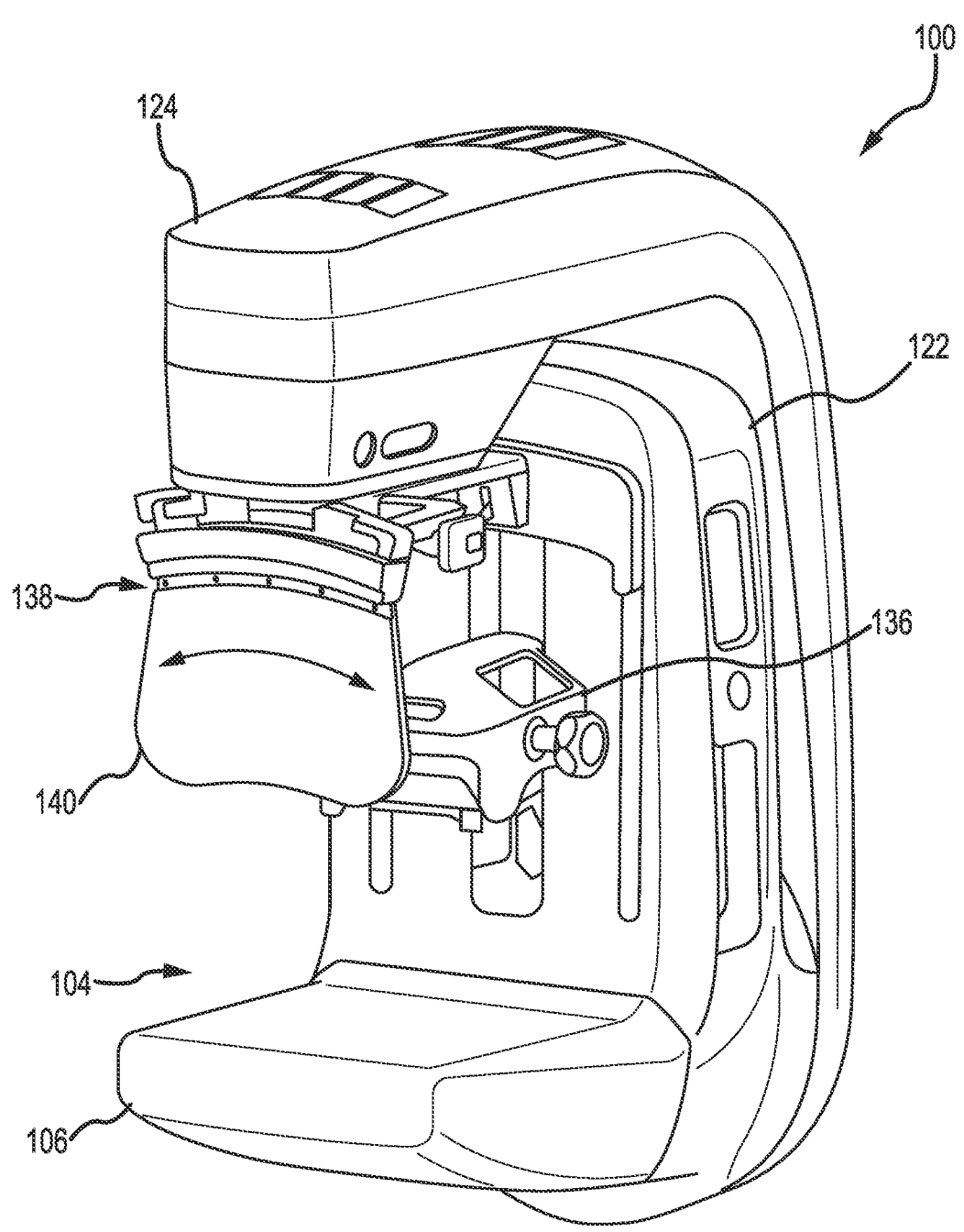
FIG. 2 is a perspective view of the imaging system of FIG. 1.

FIG. 1 is a schematic view of an exemplary imaging system 100. FIG. 2 is a perspective view of the imaging system 100. Referring concurrently to FIGS. 1 and 2, not every element described below is depicted in both figures. The imaging system 100 is configured to immobilize a patient's breast 102 for x-ray imaging (e.g., mammography, tomosynthesis, and/or wide angle imaging) via a compression arm assembly 104. In the example, the compression arm assembly 104 includes a static breast support platform 106 and a moveable compression paddle 108. The breast support platform 106 and the compression paddle 108 each have a compression surface 110 and 112, respectively, with the compression surface 112 configured to move towards the support platform 106 to compress and immobilize the breast 102. In known systems, the compression surfaces 110, 112 are exposed so as to directly contact the breast 102. The support platform 106 also houses an x-ray image receptor 114 and, optionally, a tilting mechanism 116. The compression arm assembly 104 is in a path of an imaging x-ray beam 118 emanating from an x-ray source 120, such that the beam 118 impinges on the image receptor 114.

The compression paddle 108 and the support platform 106 are supported on a first support arm 122 and the x-ray source 120 is supported on a second support arm, also referred to as an x-ray tube head 124. The support arms 122, 124 are mounted on a gantry 126. For mammography, support arms 122 and 124 can rotate as a unit about an axis 128 between different imaging orientations such as cranial-caudal (CC) and mediolateral oblique (MLO) views, so that the imaging system 100 can take a mammogram projection image at each orientation. In operation, the image receptor 114 remains in place relative to the support platform 106 while an image is taken. The compression arm assembly 104 releases the breast 102 for movement of support arms 122, 124 to a different imaging orientation. For tomosynthesis, the support arm 122 stays in place, with the breast 102 immobilized and remaining in place, while at least the tube arm 124 rotates the x-ray source 120 relative to the compression arm assembly 104 and the compressed breast 102 about the axis 128. The imaging system 100 takes plural tomosynthesis projection images of the breast 102 at respective angles of the x-ray beam 118 relative to the breast 102. Similarly for wide angle imaging, the support arm 122 stays in place, with the breast 102 immobilized and remaining in place, while at least the tube arm 124 rotates the x-ray source 120 relative to the compression arm assembly 104 and the compressed breast 102 about the axis 128. The imaging system 100 takes at least one wide angle image of the breast 102 at respective angles of the x-ray beam 118 relative to the breast 102. As such, the compression arm assembly 104 and tube head 124 may be rotated independent from each other, unless matched rotation is required or desired for an imaging procedure.

Concurrently and optionally, the image receptor 114 may be tilted relative to the breast support platform 106 and coordinated with the rotation of the second support arm 124. The tilting can be through the same angle as the rotation of the x-ray source 120, but may also be through a different angle selected such that the x-ray beam 118 remains substantially in the same position on the image receptor 114 for each of the plural images. The tilting can be about an axis 130, which can but need not be in the image plane of the image receptor 114. The tilting mechanism 116 that is coupled to the image receptor 114 can drive the image receptor 114 in a tilting motion. For tomosynthesis imaging and/or wide angle imaging, the breast support platform 106 can be horizontal or can be at an angle to the horizontal, e.g., at an orientation similar to that for conventional MLO imaging in mammography. The imaging system 100 can be solely a mammography system, a wide angle system, or solely a tomosynthesis system, or a "combo" system that can perform multiple forms of imaging. One example of such a combo system has been offered by the assignee hereof under the trade name Selenia Dimensions.

As used herein, wide angle imaging is considered to be tube head angles that are wider than typical tomosynthesis imaging, for example, angle positions above ±7° or ±7.5°. In some examples, tomosynthesis imaging may be at positions within ±7°, while in other examples tomosynthesis imaging may be at positions within ±7.5°. In an aspect, wide angle imaging includes a 60° scan of the tube head 124. Wide angle imaging can include computer tomography (CT) image acquisition, wide angle enhanced tomosynthesis (e.g., imaging angles up to and including ±30°), high energy imaging acquisitions, and the like. In some examples, the acquisitions from the wide angle imaging may be used in combination with the tomosynthesis and/or mammography acquisitions.

When the imaging system 100 is operated, the image receptor 114 produces imaging information in response to illumination by the imaging x-ray beam 118, and supplies it to an image processor 132 for processing and generating breast x-ray images. A system control and work station unit 134 including software controls the operation of the system and interacts with the operator to receive commands and deliver information including processed-ray images.

The compression paddle 108 is coupled to the support arm 122 via a paddle support 136 that is moveable linearly along the support arm 122 and used to immobilize the patient's breast 102 against the support platform 106. Additionally, the imaging system 100 includes a patient shield system 138 that is removably coupled to the support arm 122. The patient shield system 138 is disposed at least partially between the compression paddle 108 and the x-ray source 120 and includes a sliding shield 140. The shield 140 is configured to reduce or prevent patient contact with moving components (e.g., the tube head 124) during imaging procedures and to increase patient comfort around moving components of the imaging system 100. Additionally, the shield 140 guards against the patient entering the x-ray field during imaging procedures. However, the shield 140 also provides access for the technologist to position the patient's breast 102 for immobilization. As such, in combo imaging systems, like imaging system 100, the patient shield system 138 and the sliding shield 140 described herein are configured to be positioned relative to the support platform 106 such that the shield 140 can accommodate not only mammography and tomosynthesis imaging positions, but also wide angle imaging positions, while enabling access to the compression arm assembly 104 for the technologist to immobilize the patient's breast 102.

Figure 3:
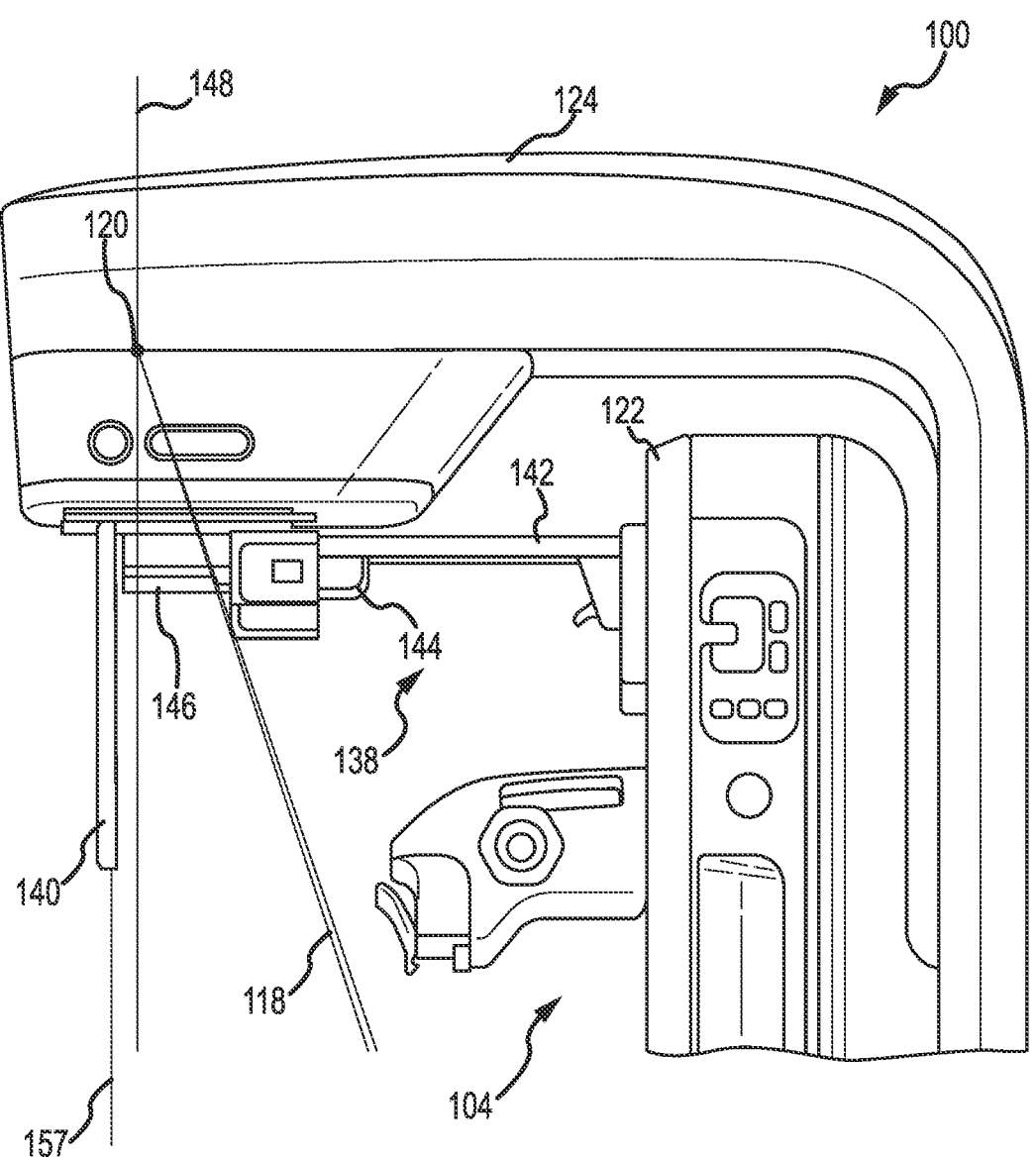
FIG. 3 is partial side view of the imaging system of FIG. 1.

FIG. 3 is partial side view of the imaging system 100. The patient shield system 138 includes an arm 142 that removably couples to the support arm 122 of the compression arm assembly 104. In the example, the arm 142 may couple to the support arm 122 via a two point attachment so that a more ridged connection is formed and to support the cantilevered configuration of the patient shield system 138. A carrier 144 is slidably coupled to the arm 142 so that the shield 140 can retract relative to the support arm 122 and the front edge of the support platform to facilitate access to the compression arm assembly 104 for the technologist. In an aspect, the arm 142 defines a longitudinal axis that the shield 140 can slide along via the carrier 144. The patient shield system 138 also includes a bracket 146 that couples the shield 140 to the carrier 144.

The x-ray tube head 124 is rotatable relative to compression arm assembly 104 such that the x-ray source 120 rotates along a tube head plane 148. The tube head plane 148 is orthogonal to the rotation axis 128 (shown in FIG. 1) of the x-ray tube head 124 and orthogonal to the breast support platform 106. The tube head plane 148 also corresponds to the front edge of the x-ray image receptor 114 (shown in FIG. 1). The x-ray source 120 emits the x-ray beams 118 towards the support platform 106 and the beams 118 are collimated to correspond to the position of the image receptor 114. As illustrated in FIG. 3, the x-ray source 120 is positioned at a 0° tube head angle relative to compression arm assembly 104. As used herein, a 0° tube head angle corresponds to the x-ray source 120 being orthogonal to the support platform 106 and within the tube head plane 148, and the tube head 124 and the compression arm assembly 104 are at the same rotational position about rotation axis 128. In an aspect, the 0° tube head angle can correspond to an MLO image position or a CC image position. At least in the 0° tube head angle position, the x-ray beam 118 passes through the patient shield system 138 when the shield 140 is being used to restrict patient access to the x-ray field because the patient shield system 138 extends through the tube head plane 148 in order to position the shield 140 between the patient and the x-ray field. As such, the bracket 146 is configured to allow the x-ray beam 118 to pass through the patient shield system 138 while reducing or preventing image artifacts from the patient shield system 138 being formed in the acquired x-ray images.

In the example, the shield 140 may be a flat plate and be positioned on the compression arm assembly 104 so that it is parallel to the tube head plane 148. By forming the shield 140 as a flat plate, the shield 140 can be moved as required or desired and remain out of the imaging field of the x-ray beams 118 even at wide angle imaging positions. As such, the bracket 146 is configured to maintain the parallel position of the shield 140 relative to the tube head plane 148 during the sliding movement of the shield 140 as described herein.

Figure 4:
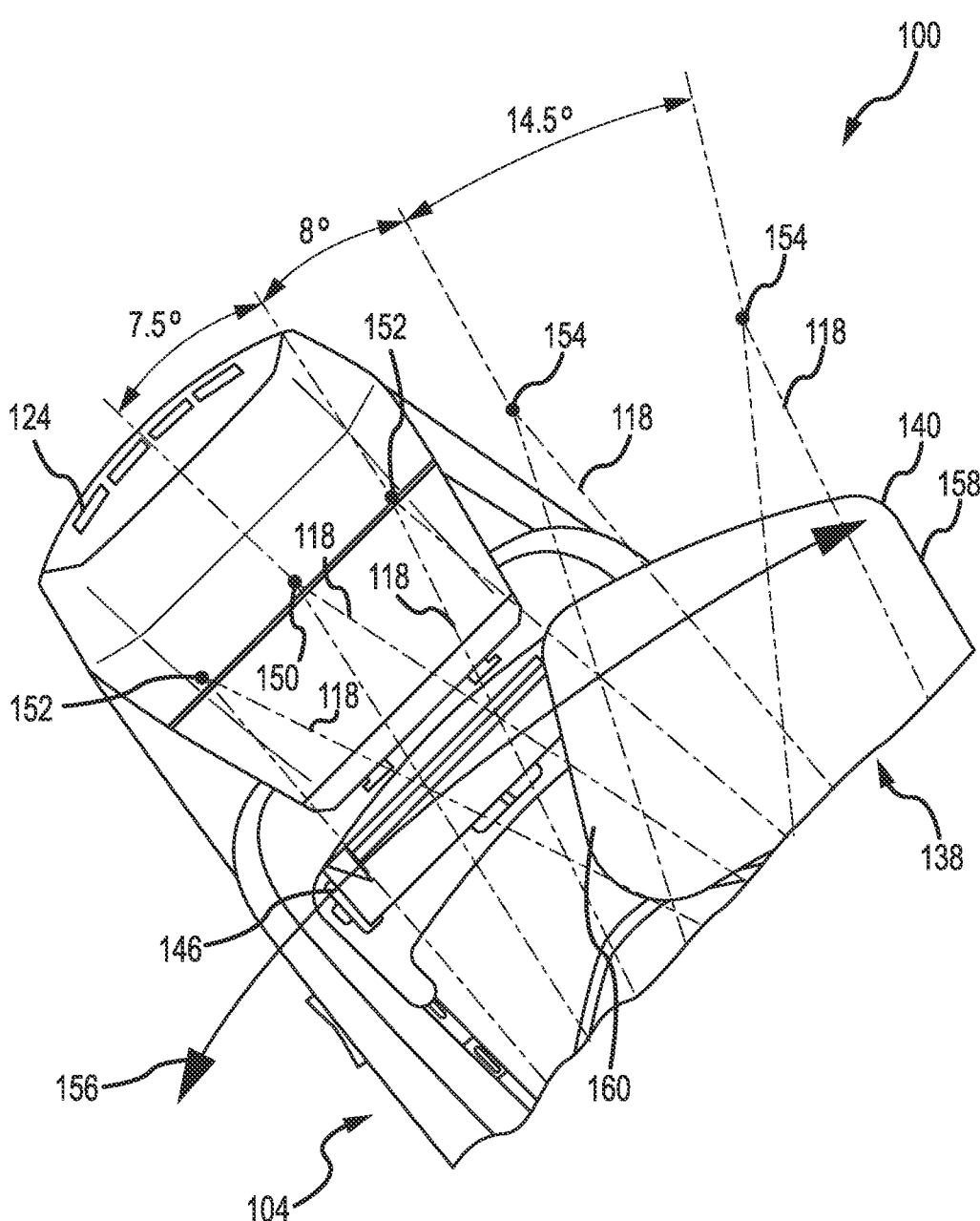
FIG. 4 is a partial front view of the imaging system of FIG. 1.

FIG. 4 is a partial front view of the imaging system 100. As illustrated in FIG. 4, the imaging system 100 is positioned in an MLO image configuration. As such, both the compression arm assembly 104 and the tube head 124 are rotated, however, the tube head 124 is still positioned at a 0° tube head angle 150 and orthogonal to the support platform 106 (shown in FIG. 1). At the 0° tube head angle 150, the imaging system 100 can acquire a MLO mammography x-ray image via an x-ray beam 118 when the imaging system 100 is operating in a mammography imaging mode. Additionally or alternatively, the imaging system 100 can operate in a tomosynthesis imaging mode and take a plurality of x-ray images via x-ray beams 118 at tomosynthesis angles 152 (which may or may not include the 0° tube head angle 150). In an aspect, the tomosynthesis angles 152 may be in a range of about 15° and between ±7.5° relative to the 0° tube head angle 150. In another aspect, the tomosynthesis angles 152 may be in a range of about 14° and between ±7° relative to the 0° tube head angle 150. The bracket 146 of the patient shield system 138 is configured to allow the x-ray beams 118 emitted at the tomosynthesis angles 152 and the 0° tube head angle 150 to pass through the patient shield system 138 such that image artifacts are reduced or prevented. When the patient is positioned for the MLO image configuration, the position and movement of the tube head 124 is typically not too close to the patient. However, when the tube head 124 is moved to wider angles, the tube head 124 and x-ray field moves closer to the patient, thereby needing the shield 140 to accommodate wider angle configurations.

The imaging system 100 is also configured to operate in a wide angle image mode and acquire one or more wide angle images via x-ray beams 118 at wide angles 154. In an aspect, the wide angles 154 may be in a range of about 60° and between ±30° relative to the 0° tube head angle 150 outside of the tomosynthesis angles 152. In some examples, angles between about ±7.5° and ±15.5° may correspond to the position of the bracket 146 and which may produce image artifacts so that these imaging angles may be eliminated from the imaging procedure. In other examples, angles between about ±7° and ±15.5° may correspond to the position of the bracket 146. As such, wide angles 154 may be between about ±15.5° and ±30° so that the x-ray beam 118 is not emitted through the projection angles that correspond to the position of the bracket 146. In other examples, the work station may be used to process image angles that have image artifacts from the bracket 146 so that the artifacts are reduced or removed. As the x-ray tube head 124 moves along the positions of the wide angles 154, the x-ray field also moves to positions that are outside of the bracket 146 of the patient shield system 138. The bracket 146 allows the shield 140 to slide relative to the carrier 144 (shown in FIG. 3) and the compression arm assembly 104 so that the shield 140 can be used to reduce or prevent the patient from encroaching into the x-ray beams 118 at these wide angles 154.

The bracket 146 defines a path of travel 156 for the shield 140 on the patient shield system 138 and the path of travel 156 is along a shield plane 157 (shown in FIG. 3) that is parallel to and offset from the tube head plane 148 (also shown in FIG. 3). This configuration enables the shield 140 to be moved and slid relative to the compression arm assembly 104 by the technologist without encroaching into the x-ray field. The path of travel 156 also has an arcuate shape so that the shield 140 does not interfere with the movement of the x-ray tube head 124 at the wide angles 154. In an aspect, the center point of the arcuate path of travel 156 is the rotation axis 128 (shown in FIG. 1) of the x-ray tube head 124. As such, both the tube head 124 and the shield 140 are selectively and independently positionable around the rotation axis 128. In an example, the path of travel 156 of the shield 140 is about 60° and corresponds to the sweep movement of the tube head 124 in all three imaging modes. In another example, the path of travel 156 of the shield 140 is at least ±30° relative to the 0° tube head angle 150. For example, the shield 140 includes two opposing edges 158, 160 and the path of travel 156 of the shield 140 enables the first edge 158 to be positioned past 30° when moved in a direction of the first edge 158 and the second edge 160 to be positioned past −30° when moved in a direction of the second edge 160. By sliding the shield 140 along an arcuate path of travel, when the imaging system 100 is in the MLO position, the distance between the support platform and the shield 140 can be maintained so that the shield 140 can more closely relate to the position of the patient.

Figure 5:
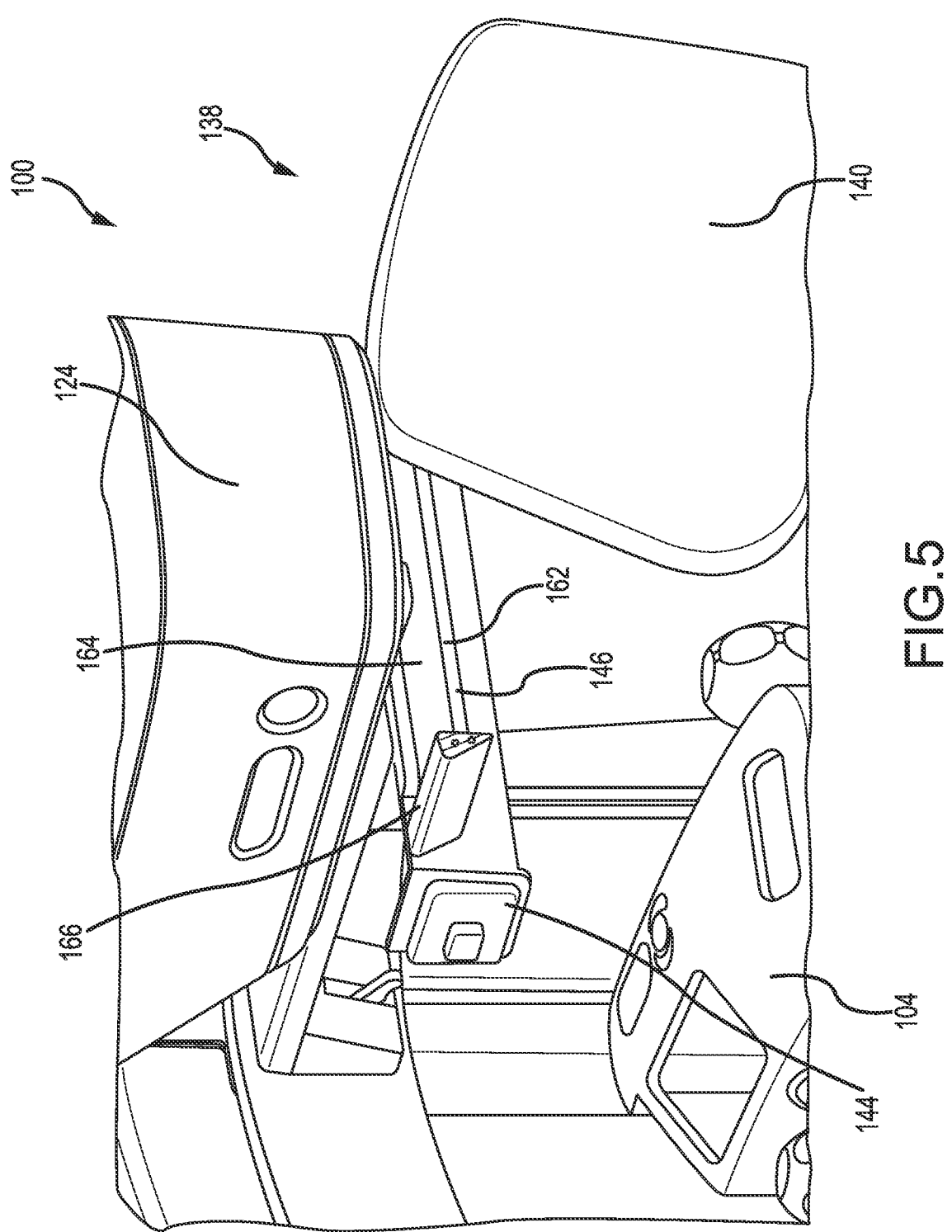
FIG. 5 is a partial perspective view of the imaging system of FIG. 1.
Figure 6:
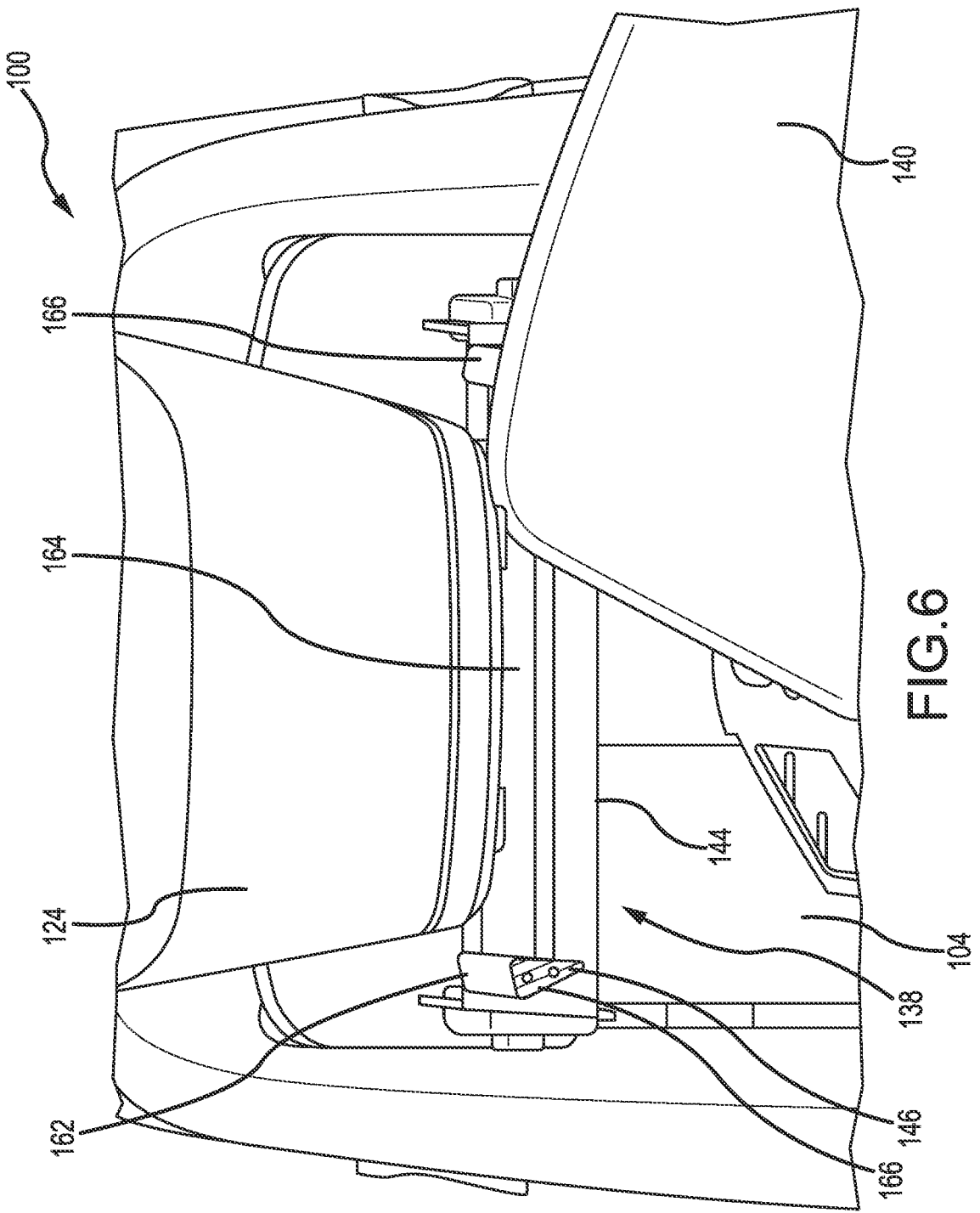
FIG. 6 is another partial perspective view of the imaging system of FIG. 1.

FIG. 5 is a partial perspective view of the imaging system 100. FIG. 6 is another partial perspective view of the imaging system 100. Referring concurrently to FIGS. 5 and 6, the bracket 146 is partially illustrated and the bracket 146 is utilized to couple the shield 140 to the carrier 144 on the patient shield system 138. The patient shield system 138 is coupled to the compression arm assembly 104 and is separate from the x-ray tube head 124. The bracket 146 includes a carrier mount 162 that is configured to couple to the carrier 144. The carrier mount 162 is supported by the patient shield system 138 so that its position on the compression arm assembly 104 can be fixed. The carrier mount 162 is only partially shown in FIGS. 5 and 6, and illustrates two different configurations for coupling the carrier mount 162 to the carrier 144.

In one example, the carrier mount 162 includes a plate 164 secured to the carrier 144. The plate 164 extends through the tube head plane 148 (shown in FIG. 3) such that the plate 164 is in the x-ray field when the tube head 124 is positioned in the mammography or tomosynthesis mode and the x-ray beams are emitted through the plate. This configuration is illustrated in FIG. 3, for example. As such, the plate 164 is formed from a radiolucent material (e.g., carbon fiber with a foam core) having a uniform thickness so as to reduce image artifacts in the x-ray images. For example, by positioning the plate 164 closer to the focal spot of the x-ray source, the plate 164 being imaged may only produce a slight attenuation in the x-ray image, which can still be used for diagnostics and/or have the attenuations reduced or eliminated during the processing of the image by the work station. The plate 164 is elongated along the path of travel 156 of the shield 140 so as to increase the engagement length of the carrier mount 162 with the shield 140 and support the cantilevered configuration of the shield 140 when moved into wide angle positions (e.g., as shown in FIGS. 5 and 6).

In another example, the carrier mount 162 includes a pair of legs 166 spaced apart from one another and secured to the carrier 144. The legs 166 extend through the tube head plane 148, however, the space between the legs 166 is open so that the bracket 146 is disposed outside of the x-ray field when the tube head 124 is positioned in the mammography or tomosynthesis mode. By spacing the legs 166 along the path of travel 156 of the shield 140, the shield 140 is supported when in the cantilever configurations. In some examples, the legs 166 may have a triangular cross-sectional shape to accommodate x-ray beams at the boundary between tomosynthesis mode and the wide angle mode while reducing the angular positions of the tube head 124 that the legs 166 may form image artifacts in. In some examples, the imaging system 100 may be configured to not take projection images at angular locations that correspond to the position of the legs 166 that extend through the tube head plane 148.

Figure 7:
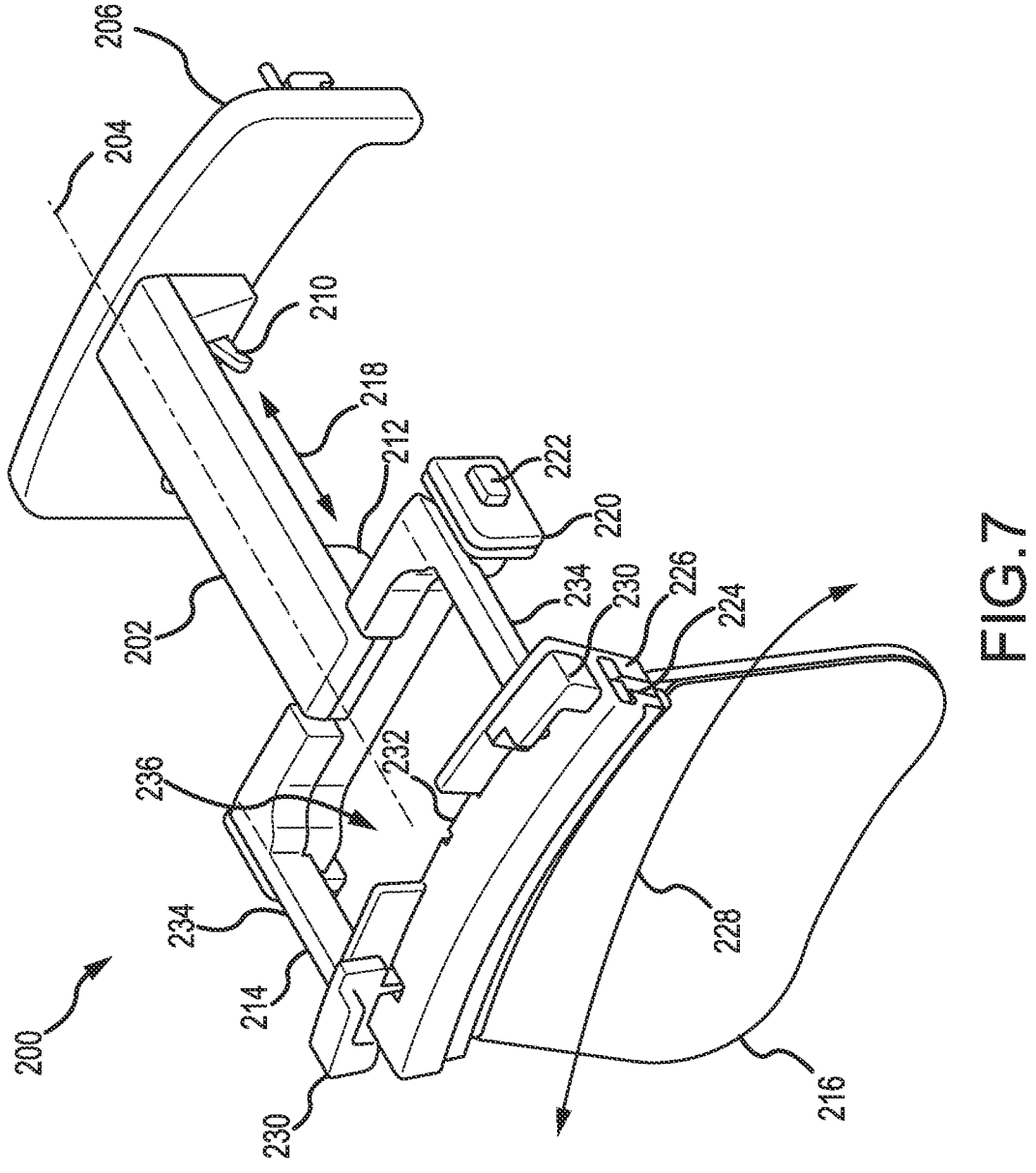
FIG. 7 is a perspective view of an exemplary patient shield system.

FIG. 7 is a perspective view of an exemplary patient shield system 200 that can be used with the imaging system 100 (shown in FIGS. 1-6). The patient shield system 200 includes an arm 202 configured to be removably couple to the support arm of the compression arm assembly. The arm 202 defines a longitudinal axis 204 and one end of the arm 202 includes an arm plate 206. The arm plate 206 releasably secures to the compression arm assembly. A locking mechanism 210 may be used to lock the position of the arm 202 on the support arm. In the example, the arm plate 206 provides a rigid two point connection to support the patient shield system 200 on the compression arm assembly.

A carrier 212 is coupled to the other end of the arm 202 and is configured to support a bracket 214 for a shield 216. The carrier 212 is slidably coupled to the arm 202 so that the carrier 212 can slide 218 along the longitudinal axis 204. The carrier 212 includes a cross-member 220 with ends that include a button 222 that facilitates positioning of the carrier 212 along the arm 202.

The bracket 214 is configured to support the shield 216 and also defines an arcuate shape path of travel for the shield 216. The shield 216 moves along a transverse plane orthogonal to the longitudinal axis 204 and the shield 216 is parallel on this transverse plane. The bracket 214 extends across the tube head plane 148 (shown in FIG. 3), and as such, is shaped and sized so that x-ray beams to pass through the patient shield system 200 in at least some imaging angles. The bracket 214 has a shield mount 224 that couples to the shield 216 and a carrier mount 226 coupled to the carrier 212. The shield mount 224 and the carrier mount 226 are engaged to allow the shield 216 to be slidingly moved 228 along the path of travel and relative to the carrier 212 and the arm 202. The carrier mount 226 is fixed to the carrier 212 and the shield mount 224 is slidable relative to the carrier mount 226 and the carrier 212. The carrier mount 226 can include a locking mechanism 230 on each side that are configured to secure the position of the shield 216 relative to the carrier 212. By placing a locking mechanism 230 on each side of the shield 216, the technologist can more easily secure the position of the shield 216 when working at either side of the patient.

The carrier mount 226 includes a support 232 configured to engage the shield mount 224 and a pair of legs 234 extending from the support 232 and configured to couple to the cross-member 220 of the carrier 212. An opening 236 is defined by the support 232, the pair of legs 234, and the carrier 212 that is sized and shaped to allow x-rays to pass through the patient shield system 200.

Figure 8:
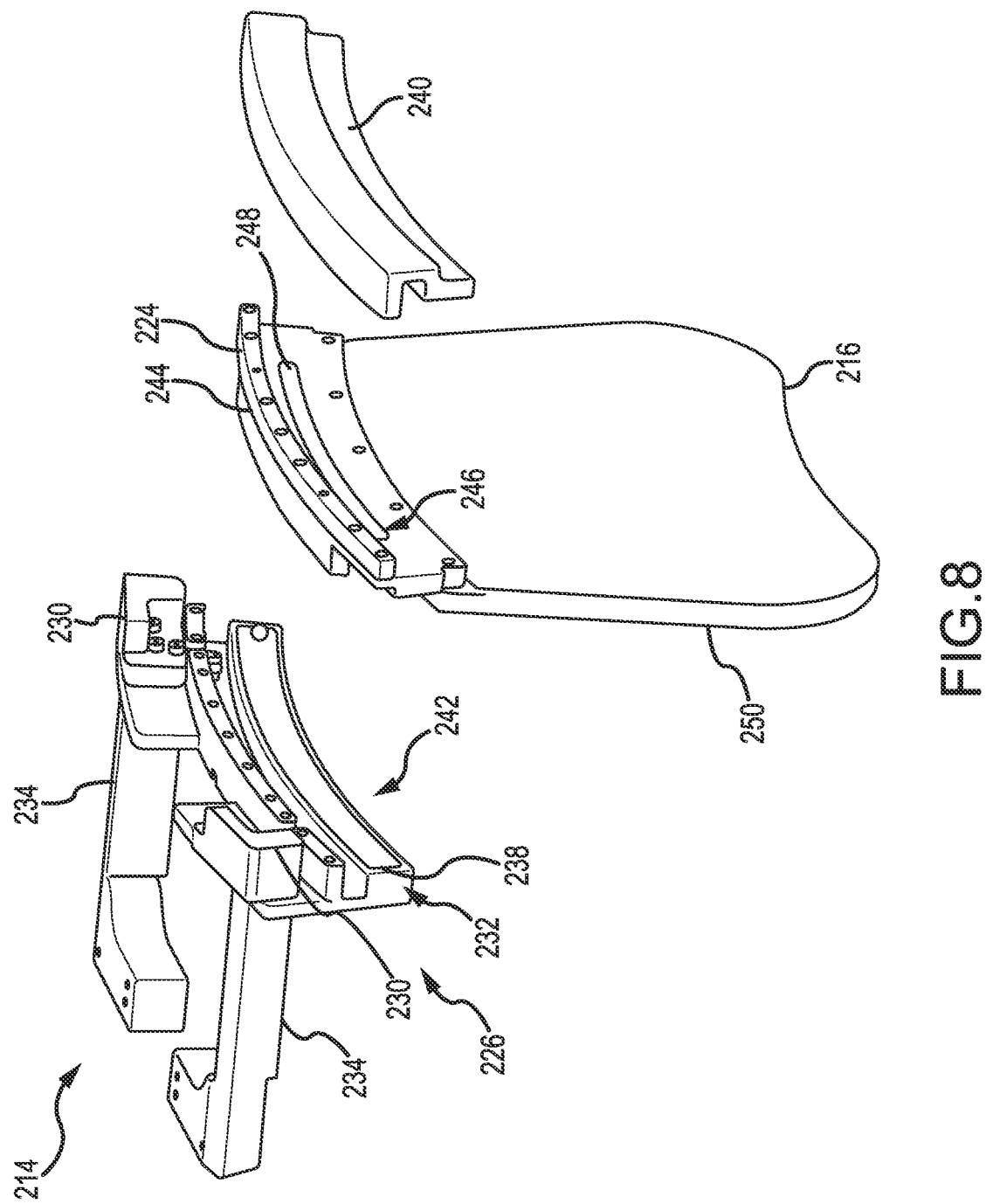
FIG. 8 is an exploded view of a bracket and a shield of the patient shield system of FIG. 7.
Figure 9:
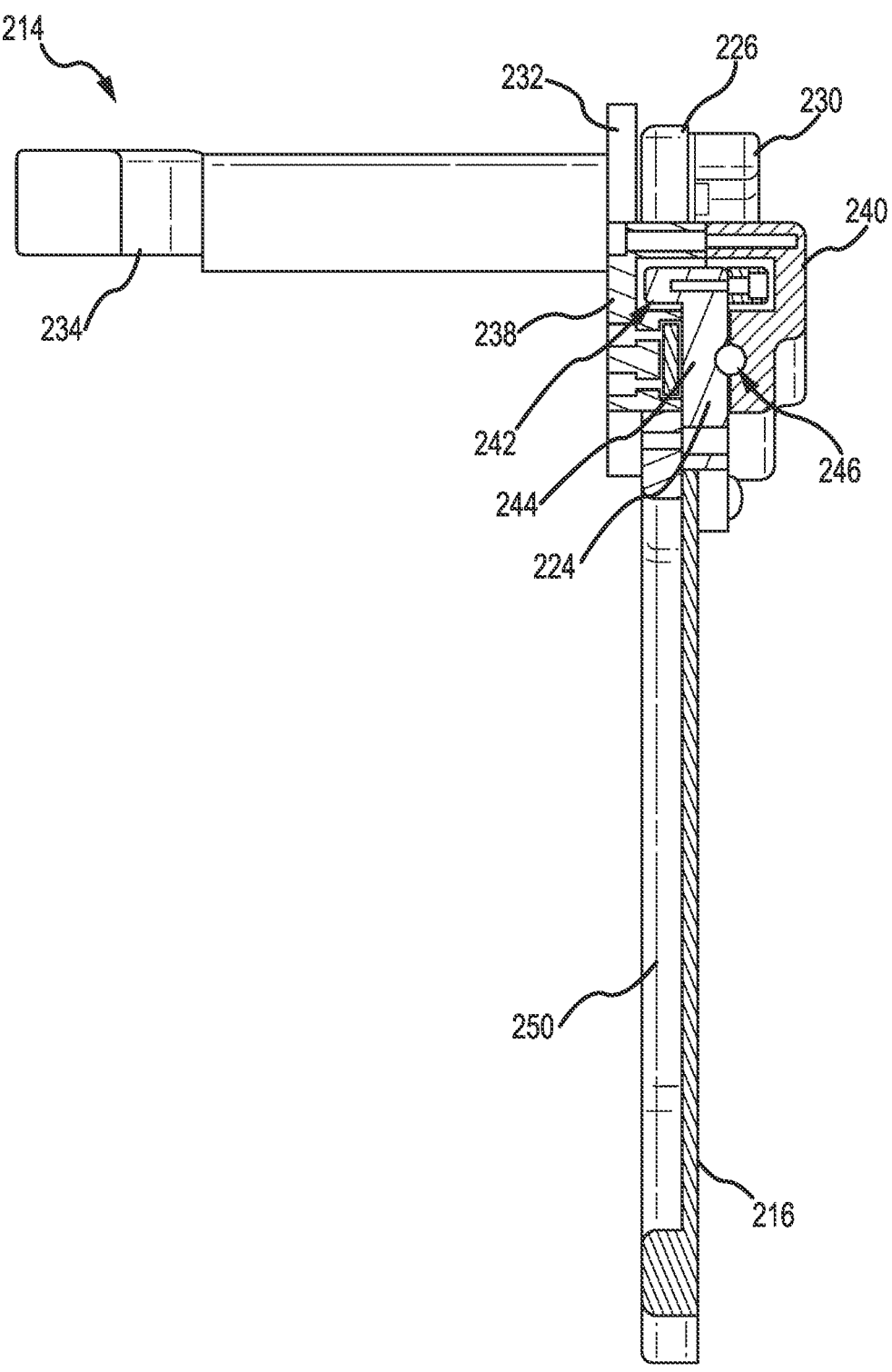
FIG. 9 is a cross-sectional view of the bracket and the shield of the patient shield system of FIG. 7.

FIG. 8 is an exploded view of the bracket 214 and the shield 216 of the patient shield system 200 (shown in FIG. 7). FIG. 9 is a cross-sectional view of the bracket 214 and the shield 216. Referring concurrently to FIGS. 8 and 9, the support 232 of the carrier mount 226 is formed from two track portions 238, 240 that couple together to form a T-shaped track 242. The shield mount 224 is coupled to the shield 216 and forms a corresponding T-shaped flange 244 that is slidingly received in the T-shaped track 242. Corresponding arcuate grooves 246 are defined in both of the shield mount 224 and the carrier mount 226 that are configured to hold a roller ball 248. The grooves 246 at least partially define the path of travel of the shield 216 and the roller ball 248 facilitates the sliding movement of the shield mount 224 relative to the carrier mount 226. In other examples, enclosed rollers may be used to facilitate the sliding movement of the shield 216. The locking mechanisms 230 are mounted on the support 232 and allow the technologist to manually lock the position of the shield 216. For example, the locking mechanism 230 may include a pin that is configured to engage into a detent within the shield mount 224.

In the example, the shield mount 224 extends across the entire length of the shield 216, but does not extend outwards from the shield 216. This configuration facilitates the technologist being able to more easily work around the patient shield system 200 and position the patient. The shield 216 may also include a frame 250 to facilitate coupling the shield 216 to the shield mount 224.

In operation, the shield 216 is positionable along the accurate path of travel by the technologist as required or desired and the locking mechanisms 230 allow for the shield 216 to be held in position for positioning the patient at the imaging system. The shield 216 has a wide range of motion to accommodate a large tube head sweep angle, and as such, large moment arms may be formed within the patient shield system 200 when the shield 216 is positioned in the furthest left or right positions. By spacing apart the legs 234 and using the support 232 to surround both sides of the shield mount 224, the bracket 214 is robust and is able to support the cantilevered positions of the shield 216, even when the patient is pressing against the shield 216 and applying a force to the patient shield system 200. Additionally, the bracket 214 extends across the entire length of the shield 216 so the shield 216 can support the patient in its extended position and without deflecting into the x-ray field of the imaging system.

Figure 10:
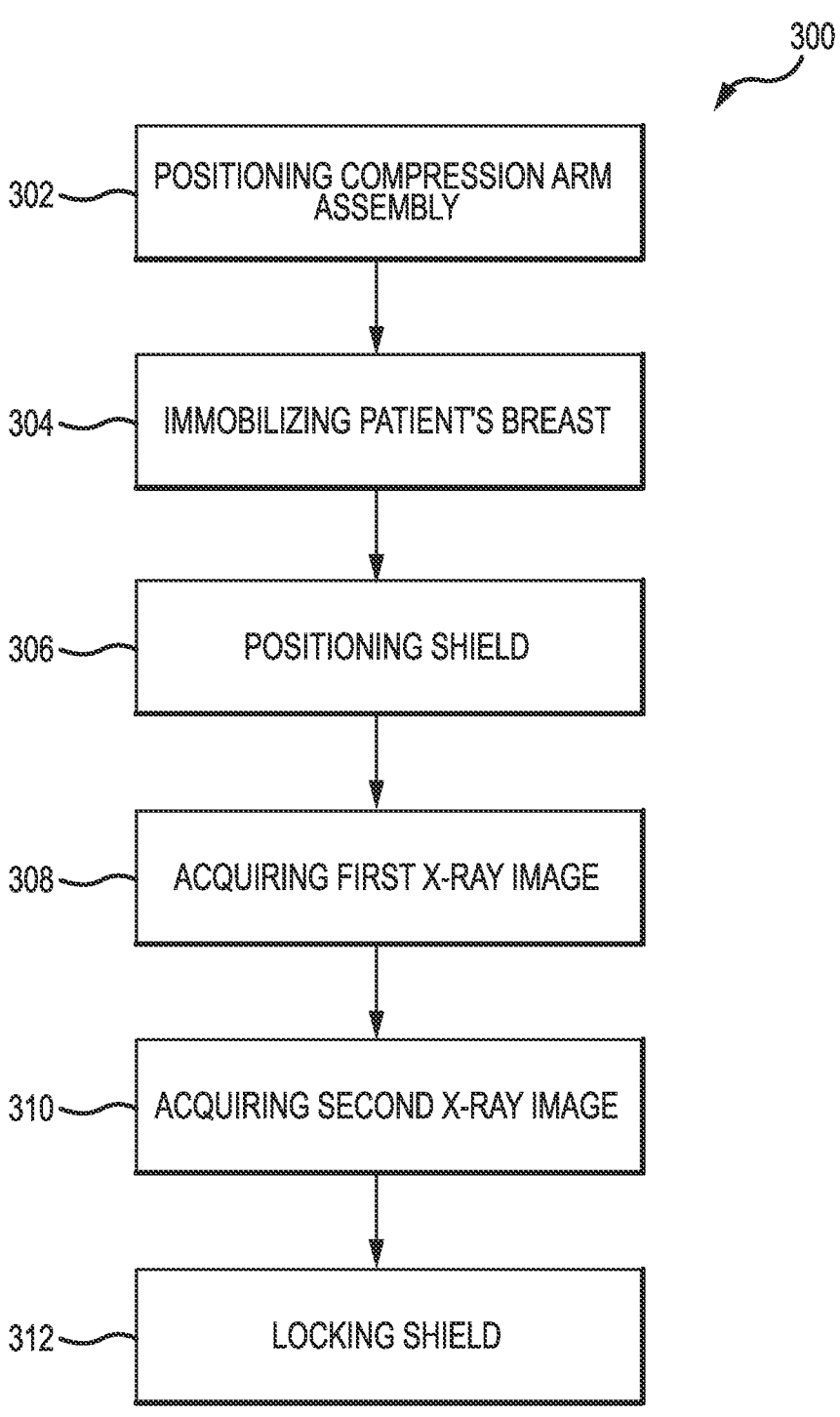
FIG. 10 depicts a flowchart illustrating a method of imaging a patient's breast.

FIG. 10 depicts a flowchart illustrating a method 300 of imaging a patient's breast. The method 300 can be performed on the imaging systems described herein or any other imaging system as required or desired. The method 300 begins with positioning a compression arm assembly (operation 302). The compression arm assembly including a support arm supporting a compression paddle, a platform, and an x-ray receptor disposed below the platform. The patient's breast is then immobilized between the compression paddle and the platform (operation 304). In some examples, positioning the compression arm assembly includes positioning the compression arm assembly in an MLO imaging position.

A shield is positioned at least partially between the patient and an x-ray field of an x-ray tube head (operation 306). The shield being coupled to the support arm by at least an arm and a carrier. The shield is movable relative to the support arm linearly along the arm via the carrier and transversely along a plane orthogonal to the arm via a bracket, and a path of travel of the shield is arcuate in shape along the transverse plane. Once the shield is positioned, one or more first x-ray images are acquired in at least one first imaging mode (operation 308). The at least one first imagining mode is at tube head angles less than or equal to ±7° relative to a 0° tube head angle. In another example, the at least one first imagining mode is at tube head angles less than or equal to ±7.5° relative to a 0° tube head angle. In an aspect, the at least one first imaging mode includes tomosynthesis imaging. In another aspect, the at least one first imaging mode includes mammography imaging. In still another aspect, the at least one first imaging mode includes tomosynthesis and mammography imaging. In yet another aspect, the second imaging mode is enhanced tomosynthesis.

One or more second x-ray images are then acquired in a second imaging mode (operation 310). The second imaging mode is at tube head angles greater than ±7.5° relative to the 0° tube head angle and the shield is positioned relative to the x-ray field of the second imaging mode. In another example, the second imaging mode is at tube head angles greater than ±7° relative to the 0° tube head angle and the shield is positioned relative to the x-ray field of the second imaging mode. In an aspect, the second imaging mode is at tube head angles greater than or equal to ±15.5° relative to the 0° tube head angle, and in this example, projection images may be eliminated for the positions that result in image artifacts being formed by the bracket of the patient shield system (e.g., between ±7.5° and ±15.5°). In some examples, the method 300 can also include locking the shield in place relative to the compression arm assembly (operation 312).

Figure 11:
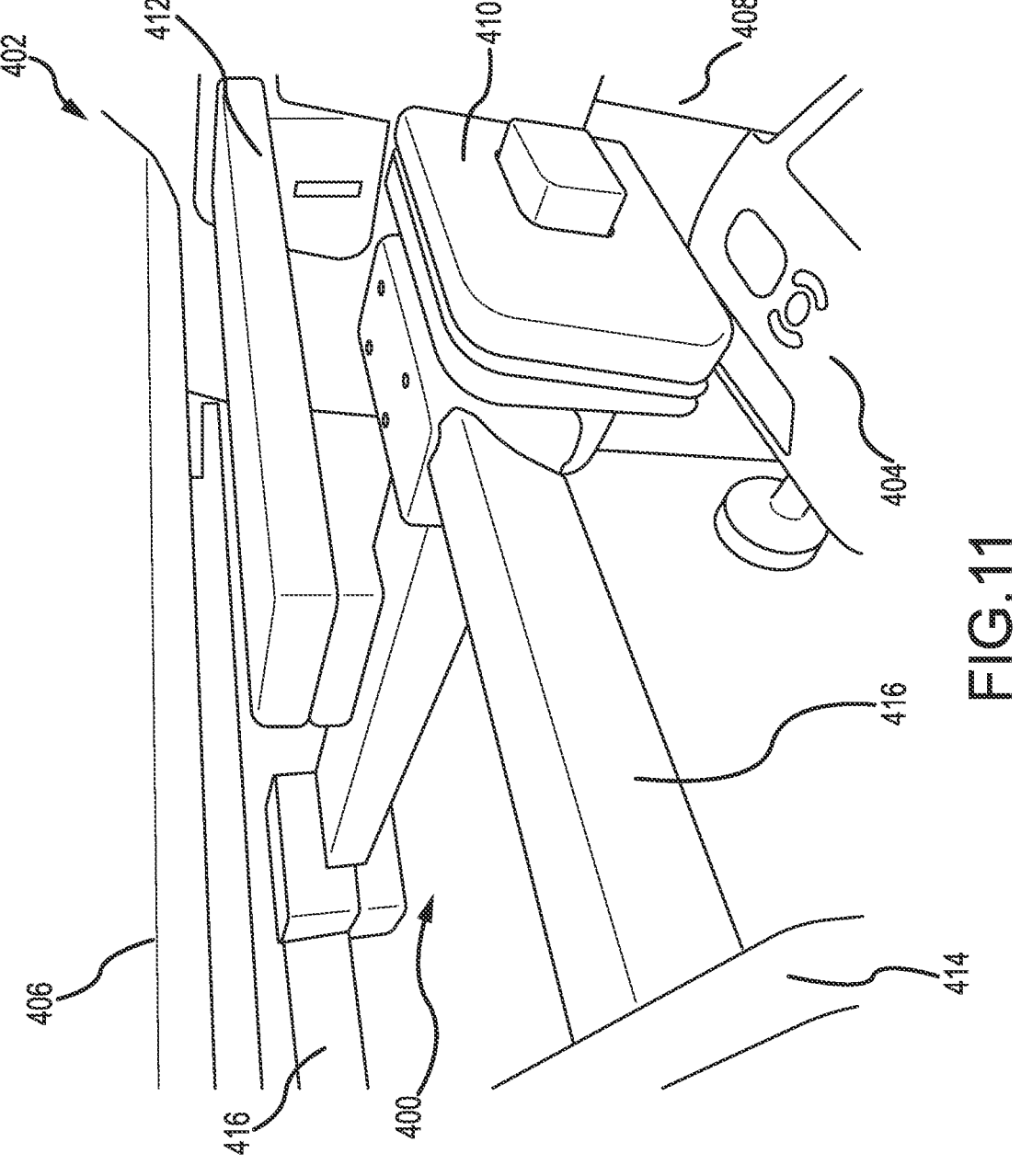
FIG. 11 is a partial perspective view a patient shield system attached to an imaging system.
Figure 12:
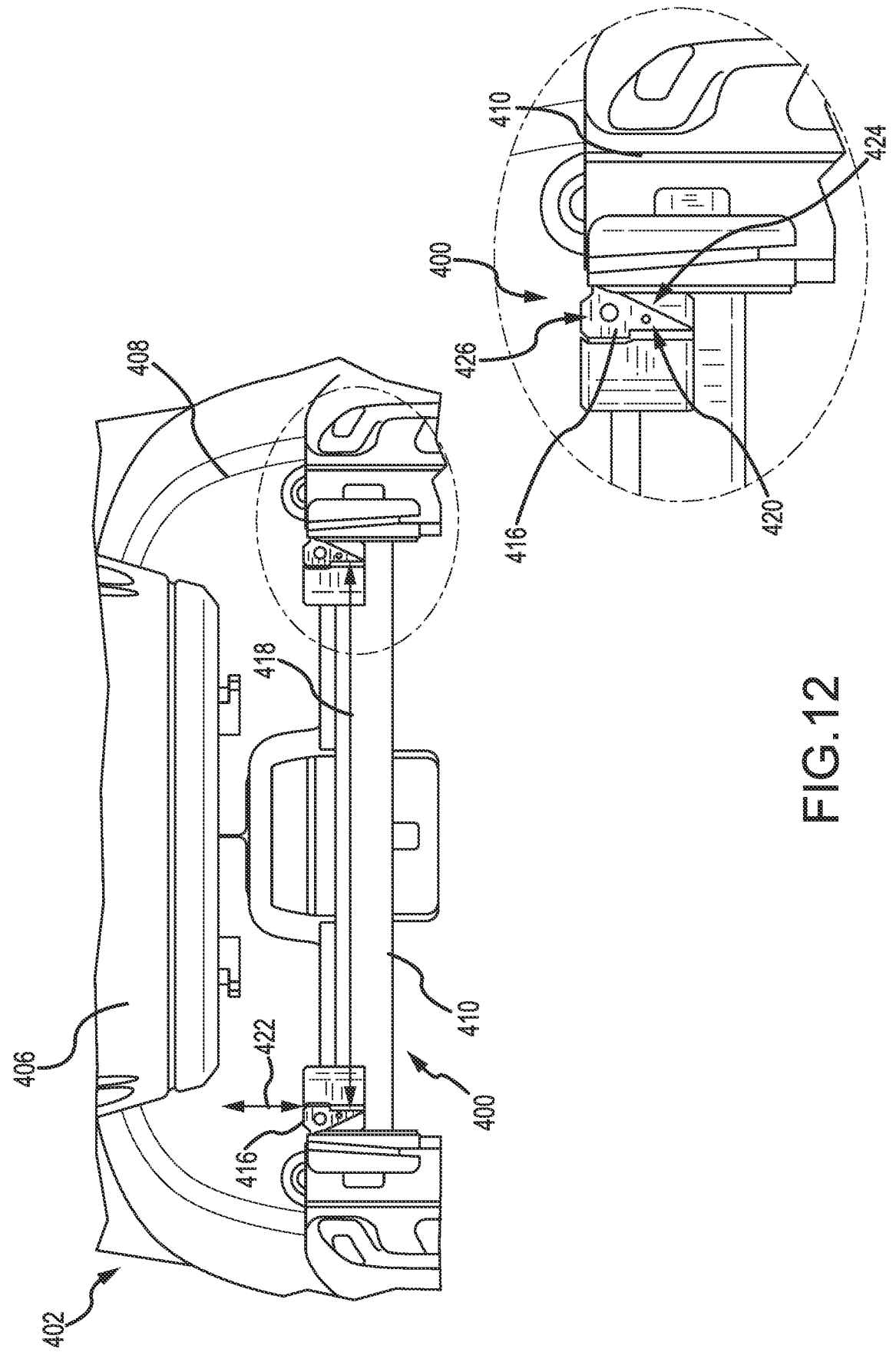
FIG. 12 is a front view of the patient shield system attached to the imaging system as shown in FIG. 11.

FIG. 11 is a partial perspective view a patient shield system 400 attached to an imaging system 402. FIG. 12 is a front view of the patient shield system 400 attached to the imaging system 402. Referring concurrently to FIGS. 11 and 12, the patient shield system 400 is disposed between a paddle support 404 and an x-ray tube head 406, and is coupled to a support arm 408. The patient shield system 400 includes a carrier 410 coupled to an arm 412. Additionally, the patient shield system 400 includes a bracket 414 configured to support a shield (not shown). The bracket 414 includes a pair of legs 416 that extend between the carrier 410 and the shield. The pair of legs 416 are spaced apart from one another by a distance 418. The spacing distance 418 enables the shield to be supported in a cantilevered configuration. Additionally, the spacing distance 418 provides an area within the patient shield system 400 that is free of any structure so that image artifacts of the legs 416 are reduced or prevented during imaging procedures.

As illustrated in FIG. 12, the tube head 406 is positioned at a 0° tube head angle. An inside surface 420 of each of the legs 416 are spaced apart 418 such that the tube head 406 can move between ±8° without the legs 416 forming image artifacts in the corresponding x-ray images. The spacing distance 418 extends in a direction that is substantially parallel to the compression surface of the breast support platform. As such, the spacing distance 418 is substantially orthogonal to x-ray beam direction when the x-ray source is at the 0° tube head angle. This spacing distance 418 enables 15° tomosynthesis scans to be performed without interference from the legs 416. Furthermore, working or positioning light emanating from the tube head 406 is not blocked by the patient shield system 400. Additionally, the legs 416 are offset in a downward direction 422 relative to the tube head 406. The offset direction 422 enables the tube head 406 to rotate relative to the patient shield system 400 without forming pinch point at the legs 416 and protecting the technologist. The offset direction 422 extends in a direction that is substantially orthogonal to the compression surface of the breast support platform. As such, the offset direction 422 is substantially parallel to the x-ray beam direction when the x-ray source is at the 0° tube head angle.

In the example, a cross-sectional profile of each of the legs 416 is substantially triangular in shape. The triangular shape is oriented in a downward direction with the inside surface 420 being oriented at the ±8° tube head angle position and an outside surface 424 being oriented at the ±15° tube head angle position. Each leg 416 also includes a top surface 426 extending between the inside and outside surfaces. As such, the patient shield system 400 is positioned on the imaging system 402 so that each leg 416 is positioned between either a −15° and −8° or a +8 and +15° tube head angle. The cross-sectional profile of the legs is configured to increase the structural strength of the legs 416 for supporting the shield and reduces or prevents image artifacts during imaging procedures at certain projection angles. For example, the size, shape, and position of the legs 416 prevents image artifacts of the legs 416 in projection angles that are outside of the −15° and −8°, and +8° and +15° tube head angle range, while the size, shape, and position of the legs 416 reduces the image artifact of the legs 416 in projection angles that are inside of the −15° and −8°, and +8° and +15° tube head angle range. Additionally, the position of each leg 416 between the −15° and −8°, and +8° and +15° tube head angle range increases the compactness of the patient shield system 400 on the imaging system 402, and thus, increases the working space for the technologist.

Figures 13, 14, 15:
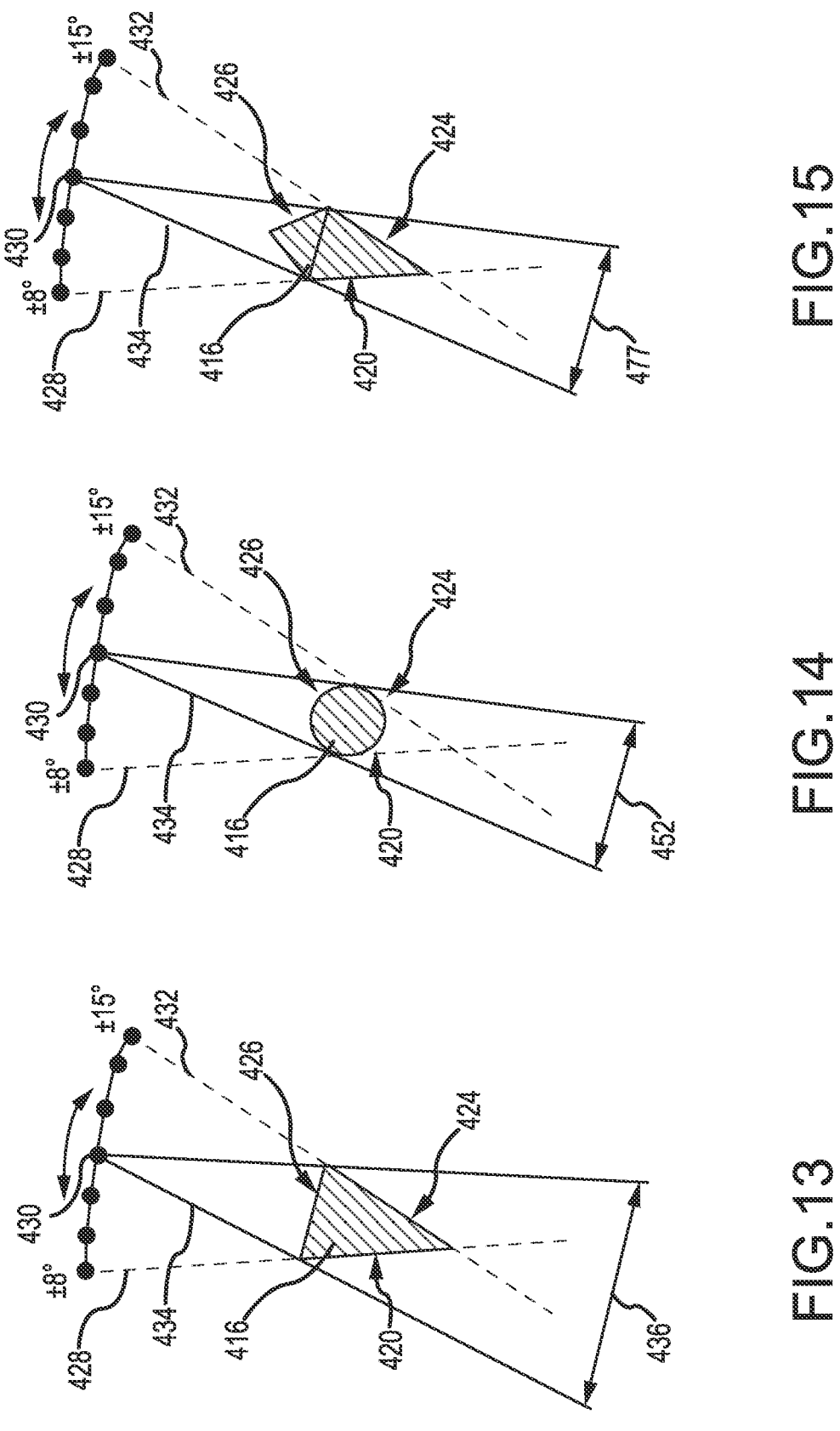
FIG. 13 is a schematic view of a leg of the patient shield system shown in FIGS. 11 and 12.
FIG. 14 is a schematic view of another leg that can be used with the patient shield system shown in FIGS. 11 and 12.
FIG. 15 is a schematic view of another leg that can be used with the patient shield system shown in FIGS. 11 and 12.

FIG. 13 is a schematic view of the leg 416 of the patient shield system 400 (shown in FIGS. 11 and 12). In the example, the leg 416 has a cross-sectional profile of a triangle with the inside surface 420 being aligned with a ±8° tube head angle. In an aspect, the ±8° angle is based on aligning 428 the x-ray imaging area outer edge of an x-ray source 430 with one edge (e.g., the closer edge) of the x-ray detector (not shown) so that the leg 416 is outside of the imaging area and no image artifacts of the leg 416 are formed at the ±8° projection angle. The outside surface 424 is aligned with the ±15° tube head angle. In an aspect, the ±15° angle is based on aligning 432 the x-ray imaging area outer edge of the x-ray source 430 with the other edge (e.g., the further edge) of the x-ray detector so that the leg 416 is outside of the imaging area and no image artifacts of the leg 416 are formed at the ±15° projection angle. As such, the leg 416 only generates an image artifact when the x-ray tube head angle is between −15° and −8°, and +8° and +15° because an x-ray source 430 shoots an x-ray beam 434 through at least a portion of the leg 416.

A shadow width 436 of the image artifact is based at least partially on the top surface 426 of the leg 416. Accordingly, a larger top surface 426 creates a larger shadow width 436 than a smaller top surface. However, smaller top surfaces 426 correspond to less structural strength of the leg 416 than a larger top surface 426 because of the cross-sectional area reduction of the leg 416. Accordingly, the cross-sectional shape of the leg 416 can take on other shapes so as to increase performance of the patient shield system. Furthermore, in the examples described herein, the shadow width 436 of the leg 416 is of a width so that when image artifacts are generated in two adjacent projection angles, the image artifacts of the leg 416 do not overlap in image position so that the projection images can be used in reconstruction. Two examples of other cross-sectional shapes are described further below in reference to FIGS. 14 and 15, however, any other shape can be utilized as required or desired.

During operation of the imaging system, the x-ray tube head rotates so as to take a plurality of projection images of the patient's breast. In some examples, the x-ray source 430 can rotate with the tube head between ±60° and acquire projection images at predetermined angular rotations. In an aspect, projection images may be acquired at approximately every 1°. Accordingly, when the x-ray source 430 is at tube head angles between −15° and −8° or +8° and +15° and corresponding to the position of the leg 416, the x-ray beam 434 is intentionally shot through the leg 416 and image artifacts are intentionally formed in the projection image. Thus, the structure and position of the leg 416 within the patient shield system both reduces the number of projection angles that include image artifacts of the leg 416 and reduces the width of the image artifact shadow within the projection images. In an aspect, when the x-ray source 430 is at a ±8° tube head angle, an image artifact of the leg 416 is not generated during imaging. In another aspect, when the x-ray source 430 is at a ±15° tube head angle, an image artifact of the leg 416 is not generated during imaging.

FIG. 14 is a schematic view of another leg 450 that can be used with the patient shield system 400 (shown in FIGS. 11 and 12). Certain components are described above, and thus, not necessarily described further. In this example, the leg 450 is positioned on the imaging system such that it is between the −15° and −8° or +8° and +15° tube head angle and similar to as described above. However, the leg 450 has a cross-sectional profile of a circle. The circular perimeter is sized such that the inside surface 420 maintains alignment with the ±8° tube head angle, while the outside surface 424 maintains alignment with the ±15° tube head angle. The top surface 426 is smaller on the circular perimeter, and as such, a shadow width 452 that is generated by the leg 450 is reduced and is smaller than when compared with the triangle shape example described above in reference to FIG. 13. By shaping and sizing the leg 450 to reduce image artifact size, more information can be obtained via the projection imaging procedures. In an aspect, the size of the circular perimeter is based on being inscribed in the triangle shape shown in FIG. 13 (e.g., the circular perimeter being tangential to each of the sides of the triangle).

FIG. 15 is a schematic view of another leg 475 that can be used with the patient shield system 400 (shown in FIGS. 11 and 12). Certain components are described above, and thus, not necessarily described further. In this example, the leg 475 is positioned on the imaging system such that it is between the −15° and −8° or +8° and +15° tube head angle and similar to as described above. However, the leg 475 has a cross-sectional profile of a quadrilateral and a diamond-type shape. The quadrilateral perimeter is sized such that the inside surface 420 maintains alignment with the +8° tube head angle, while the outside surface 424 maintains alignment with the ±15° tube head angle. The top surface 426 has a similar size to the circular perimeter described above, and as such, a shadow width 477 that is generated by the leg 475 is reduced and is smaller than when compared with the triangle shape example described above in reference to FIG. 13. In this example, the shadow width 477 can be substantially equal to the shadow width of the circle described above in reference to FIG. 14. By shaping and sizing the leg 475 to reduce image artifact size, more information can be obtained via the projection imaging procedures. In an aspect, the size of the diamond shape is based on the circular perimeter shown in FIG. 14 being inscribed in the diamond such that the circular perimeter is tangential to each of the sides of the quadrilateral. It should be appreciated that other cross-sectional shapes of the leg are also contemplated herein, such as, polygonal, oval, and the like.

Figures 16, 17:
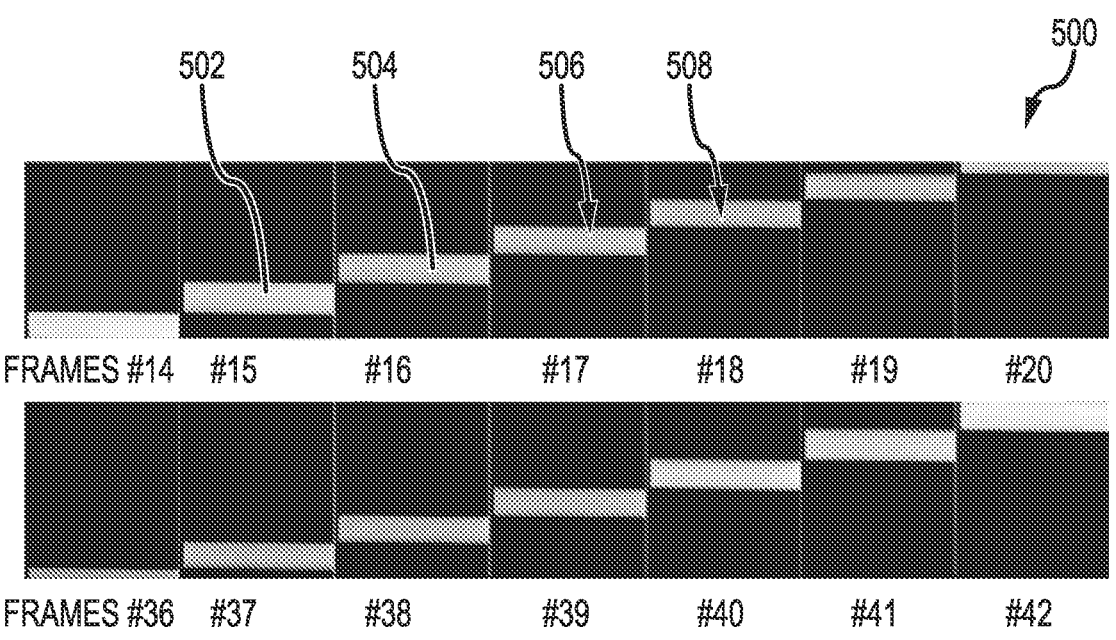
FIG. 16 depicts projection images from an imaging system shot through a leg of a patient shield system.
FIG. 17 depicts reconstruction images from the projection images of FIG. 16.

FIG. 16 depicts a plurality of projection images 500 from an imaging system shot through a leg 502 of a patient shield system. As described above, the imaging system described herein can operate in a tomosynthesis imaging mode and/or an enhanced or wide-angle tomosynthesis mode. During a tomosynthesis scan, the tube head rotates relative to the patent's breast and, in aspects, can acquire projection images 500 at predetermined angles between ±60° tube head angles. In one example, the imaging system is configured to acquire 57 projection images between the ±30° tube head angles. Because the legs of the patient shield system are disposed between the −15° and −8°, and +8° and +15° tube head angles, at least some of these 57 projection images include image artifacts 504 generated by the pair of legs 502 of the patient shield system extending across the x-ray beam. FIG. 16 illustrates frames 14-20 of the projection images shot though one of the pair of legs 502, while frames 36-42 correspond to the projection images shot through the other one of the pair of legs 502.

As described above, the legs 502 are shaped and sized so that at each projection angle that shoots x-ray beams through the leg 502, the corresponding image artifact 504 that is in the projection image does not overlap with the adjacent image. For example, a top edge 506 of the image artifact 504 shown in frame 17 does not overlap with a bottom edge 508 of the image artifact 504 shown in frame 18 when the frames are placed over one another. By preventing image artifact overlap between projection images, the greater the number of frames can be used during tomosynthesis reconstruction. In an aspect, if image artifacts do overlap between projection images, those corresponding frames may not be used for reconstruction. In some examples, the tomosynthesis reconstruction performed with the projection images may discard and not use the images having the image artifact 504 of the leg (e.g., projection images between the −15° and −8°, and +8° and +15° tube head angles). However, discarding all of the projection images between the −15° and −8°, and +8° and +15° tube head angles may reduce the quality of the reconstructed image(s). As such and in other examples, the imaging system may still use the projection images that contain the image artifact 504 of the leg during reconstruction by performing imaging corrections.

In the example, the image processor (e.g., the image processor 132 shown in FIG. 1 that includes memory and processor(s)) of the imaging system is used to identify the location of the image artifact 504 within each projection image, segment out the image artifact 504, and reconstruct the plurality of projection images 500 into a tomosynthesis reconstruction based on the processed and segmented projection images. For example, the image processor can identify the top and bottom edges 506, 508 of the image artifact 504 within each projection image. Once the location of the image artifact 504 is identified, the image artifact location is segmented out and replaced with a uniform background. In an aspect, the location of the image artifact 504 can be performed by pixels, and the pixels of the image artifact 504 are replaced by a background value that is uniform and provides no image data. It should be appreciated that segmentation can be performed in either the spatial (e.g., pixel) domain or a frequency domain as required or desired. By removing the image artifact values in the projection images, reconstruction of the processed tomosynthesis images can be performed without shadows being formed in the reconstruction as shown in FIG. 17 as described below.

FIG. 17 depicts reconstruction images 510, 512 from the projection images 500 (shown in FIG. 16). When back-projection reconstruction is performed on the projection images 500 without image artifact correction, shadows 514 are formed in the reconstruction image 510. These shadows 514 are undesirable and reduce the quality of the reconstruction image 510. In contrast, when imaged artifacts are corrected (e.g., via the process described above), when back-projection reconstruction is performed on the segmented projection images 500, shadows are not formed in the reconstruction image 512. As such, the reconstruction image 512 is of better quality if reconstruction is performed after the image artifacts of the legs are segmented out.

With continued reference to FIG. 16, when the number of projection images 500 that are used for reconstruction is reduced, the performance and accuracy of the tomosynthesis scan is reduced. Accordingly, the size, shape, and position of the legs 502 of the patient shield system reduce the number of projection images 500 that include image artifacts 504 from the legs 502. This increases the performance and accuracy of the tomosynthesis scan. Additionally, by continuing to shoot through the legs 502 with the x-ray beam, and then correcting the resulting projection images 500 further increases the performance and accuracy of the tomosynthesis scan by increasing the imaging data used for reconstruction. Imaging performance is increased by using, for example, 85% of a projection image (e.g., with the image artifact 504 segmented out), when compared to removing the projection image entirely if the image artifact 504 is contained therein.

In some examples, the projection images 500 can also have other components of the imaging system show up during imaging and on the frames. For example, these components can be a portion of the collimator, the x-ray detector, or the like. In some aspects, when the image artifact 504 is proximate the detector edges and only partially imaged (e.g., frames 14, 20, 36, and 42), it can be difficult to identify the top or bottom edges 506, 508 of these artifacts because of the other components of the imaging system. As such, the image processor can further increase accuracy of the image artifact correction process by generating a fitting curve to either the top or bottom edges 506, 508 in the frames that show the entire image artifact 504 (e.g., frames 15-19 and 37-41), and then determining the top edge 506 or the bottom edge 508 of the image artifact 504 that is only partially shown based on the fitting curve and prior to segmenting out the image artifact 504.

In order to generate a fitting curve, the image processor identifies a location of the top edge 506 of the image artifact 504 in two or more frames that show the entire image artifact 504. These frames can be, for example, frames 15-19 or frames 37-41 illustrated in FIG. 16. Based on the fitting curve of the top edge 506, the image processor can determine the top edge 506 in frames 14 or 36. Similarly, the image processor identifies a location of the bottom edge 508 of the image artifact 504 in two or more frames that show the entire image artifact 504. These frames can be, for example, frames 15-19 or frames 37-41. Based on the fitting curve of the bottom edge 508, the image processor can determine the bottom edge 508 in frames 20 or 42. While the above example describes a fitting curve based on edge location of the image artifact 504, it should be appreciated that other fitting curves can be used as required or desired. For example, a fitting curve based on area location of the image artifact 504 can be used. The image processor can also account for magnification differences in each projection image (e.g., distance of the x-ray source from the receptor) as the tube head angle changes and as required or desired.

Figure 18:
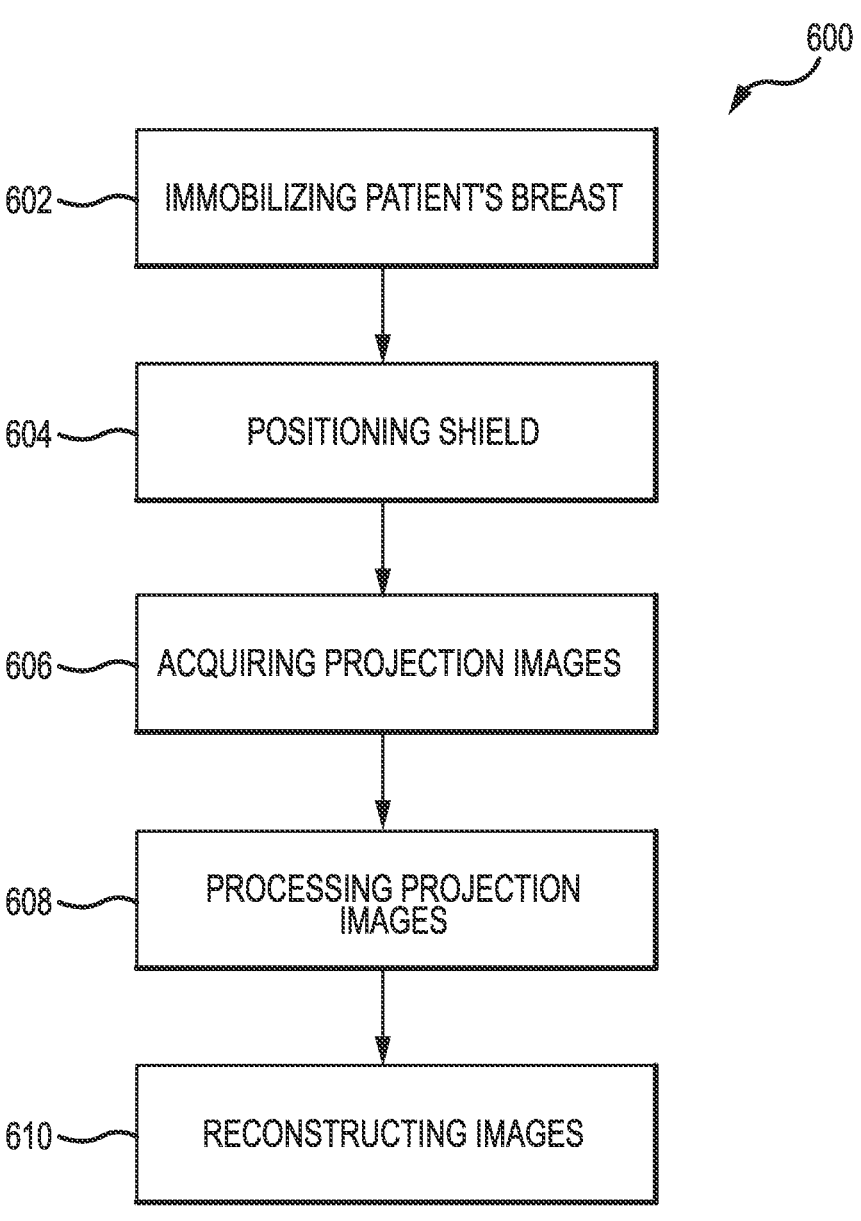
FIG. 18 depicts a flowchart illustrating another method of imaging a patient's breast.

FIG. 18 depicts a flowchart illustrating another method 600 of imaging a patient's breast. The method 600 can be performed on the imaging systems described above or any other imaging system as required or desired. The method 600 begins with immobilizing the patient's breast in a compression arm assembly (operation 602). The compression arm assembly includes a support arm supporting a compression paddle, a platform, and an x-ray receptor disposed below the platform. Additionally, a shield is positioned at least partially between the patient and an x-ray field of an x-ray tube head (operation 604). The shield is positioned on one side of a tube head plane with at least one leg supporting the shield and extending across the tube head plane.

A plurality of x-ray projection images of the patient's breast are acquired during tomosynthesis imaging (operation 606). At least two of the plurality of x-ray projections include an image artifact from the at least one leg, and the at least one leg is shaped and sized such that a location of the image artifact within the at least two x-ray projection images do not overlap with one another. In an aspect, acquiring the at least two x-ray projection images includes emitting x-ray exposures between a −15° and −8° and/or +8° and +15° tube head angle and shooting through the leg of the patient shield.

The at least two x-ray projection images are processed to segment out the image artifacts (operation 608). In some examples, processing the projection images includes identifying a location of the image artifact within the image and segmenting the image artifact with a background value. The location identification of the image artifact can include determining a position of two outermost edges of the image artifact. By determining the outmost edge position of the image artifact, the method can include processing an x-ray projection image having a partial image artifact of the at least one leg. Based on the determined position of at least one of the two outermost edges, a fitting curve can be generated such that an edge of the partial image artifact is determined from the at least two x-ray projection images having two outermost edges. Accordingly, processing of partial image artifacts have an increased accuracy.

Based on the processed at least two x-ray projection images, one or more tomosynthesis images are then reconstructed (operation 610). This reconstruction can be performed using back-projection in a spatial domain or in a frequency domain as required or desired.

Figure 19:
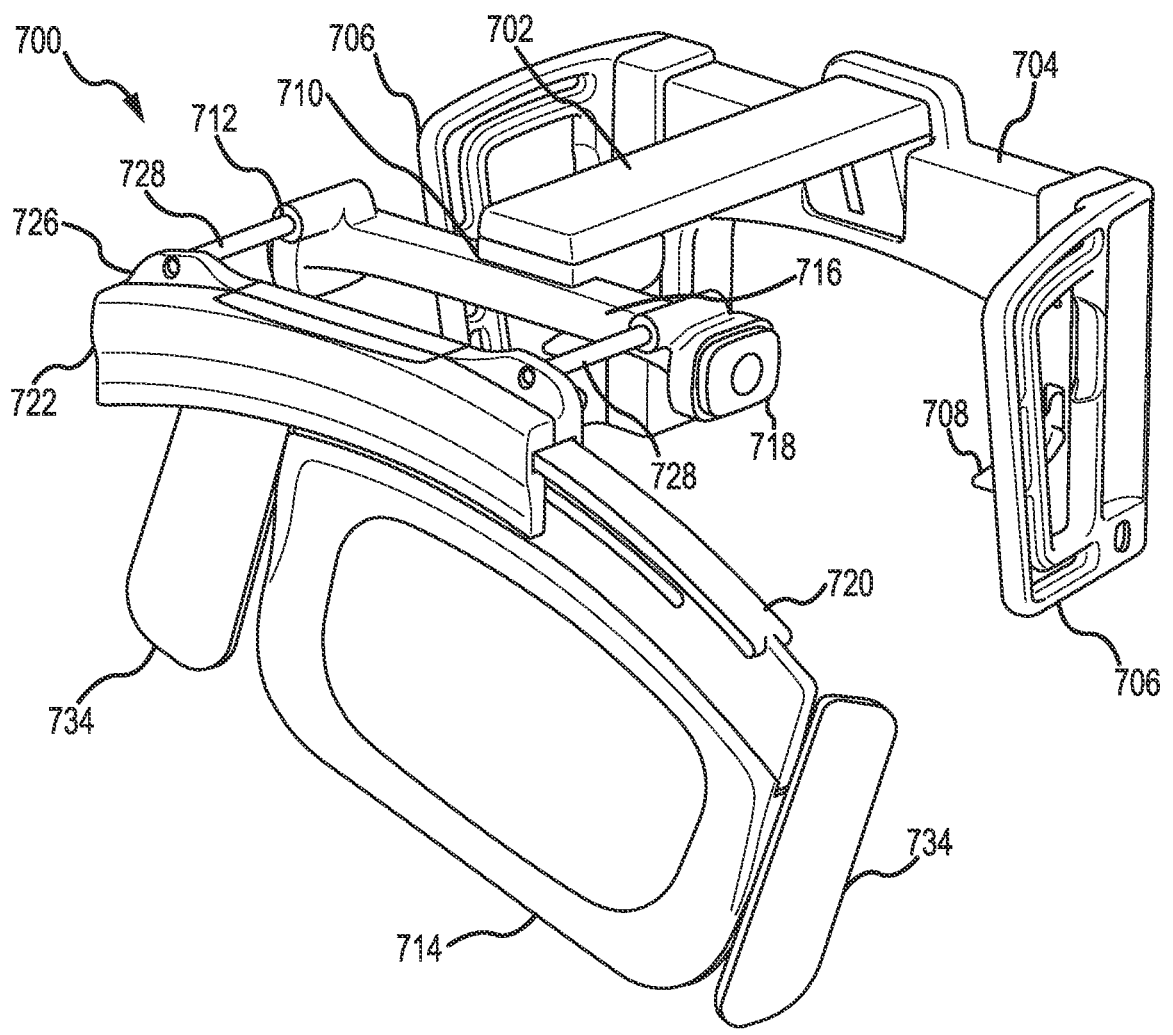
FIG. 19 is a perspective view of another patient shield system.
Figure 20:
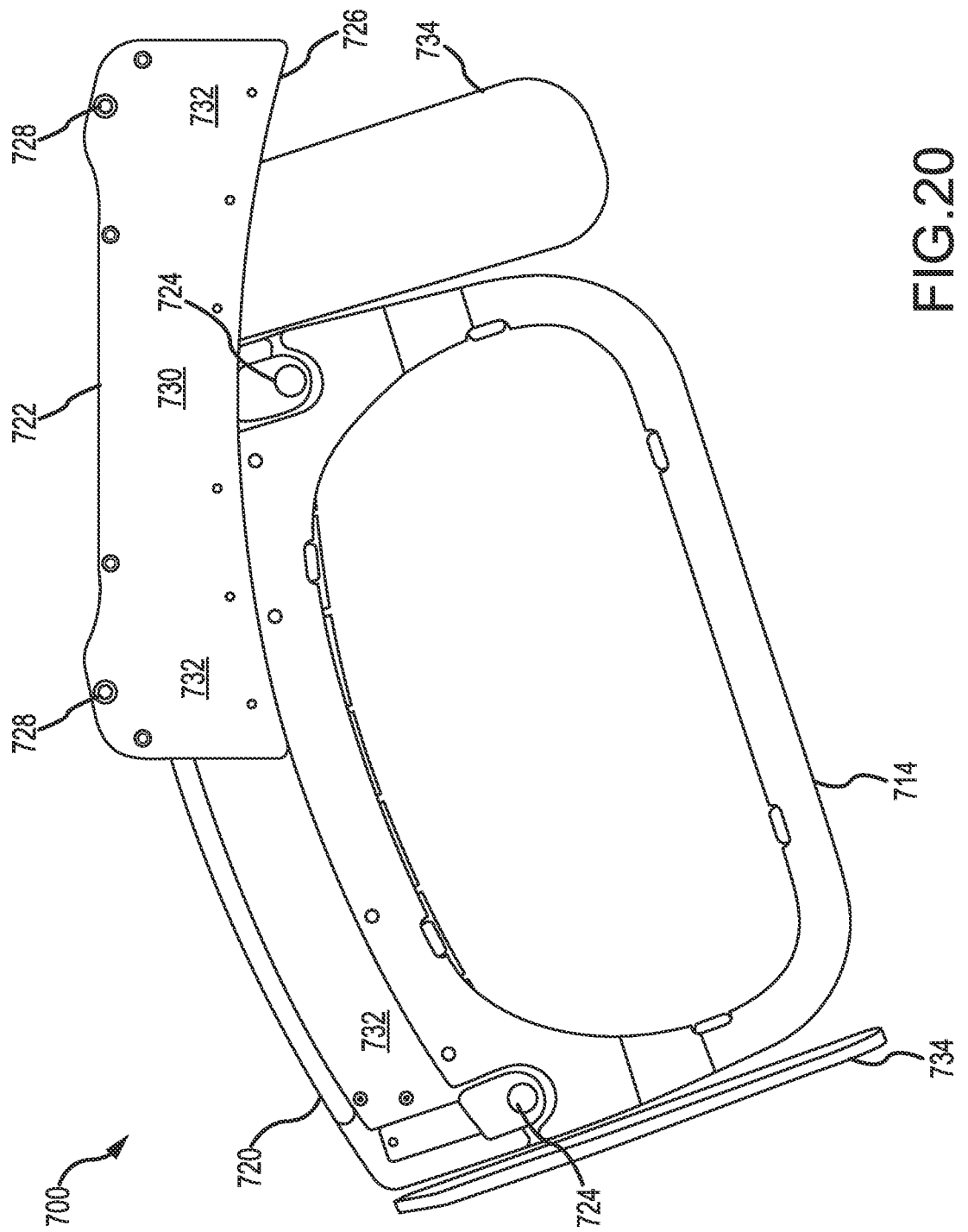
FIG. 20 is a rear view of the patient shield system shown in FIG. 19.

FIG. 19 is a perspective view of another patient shield system 700. FIG. 20 is a rear view of the patient shield system 700. Referring concurrently to FIGS. 19 and 20, the patient shield system 700 is configured to be used with the imaging system 100 (shown in FIGS. 1-6) and functions similar to the examples described above. The patient shield system 700 includes an arm 702 having an arm plate 704 that is configured to releasably secure to the compression arm assembly of the imaging system 100. In this example, the arm plate 704 may include one or more handles 706 and a locking mechanism 708 as required or desired. A carrier 710 is coupled to the other end of the arm 702 and is configured to support a bracket 712 for a shield 714. The carrier 710 is selectively slidable along the arm 702. The carrier 710 includes a cross-member 716 with ends that include a button 718 to facilitate positioning of the carrier 710 along the arm 702.

The bracket 712 is configured to support the shield 714 and enable the shield 714 to be selectively positioned on the imaging system 100 for high-angle imaging procedures as described herein. The bracket 712 includes a shield mount 720 that couples to the shield 714 and a carrier mount 722 coupled to the carrier 710. In the example, the carrier mount 722 defines a track and the shield mount 720 is configured to slide within the track. The carrier mount 722 may include one or more slide bearings to facilitate the movement of the shield mount 720 (e.g., top, bottom, and/or side slide bearings). The slide bearings may be rollers as described above. In other examples, the slide bearings may be V-shaped rollers (e.g., rollers with an annular V-shaped groove) supported by the carrier mount 722 with a corresponding track formed in the shield mount 720. In yet other examples, the shield mount 720 may support the V-shaped rollers while the carrier mount 722 defines the corresponding track.

At the rear of the shield mount 720, the patient shield system 700 may include a locking mechanism 724 at each side of the shield 714 configured to secure the position of the shield mount 720 and the shield 714 relative to the carrier mount 722. In an example, the locking mechanisms 724 may be a pair of levers coupled via a biasing rod that exerts a friction force against the carrier mount 722. This configuration enables one-handed positioning of the shield 714 by the technologist when holding the patient shield 714. In other examples, the locking mechanisms 724 can have any other structure that enables the shield 714 to function as described herein.

The carrier mount 722 includes a support 726 engaged with the shield mount 720 and a pair of legs 728 extending from the support 726 and coupled to the cross-member 716 of the carrier 710. In this example, the pair of legs 728 are substantially cylindrical and have a circular cross-sectional profile so as to reduce image artifact side during imaging procedures and similar to the leg described above in reference to FIG. 14.

In some examples, the carrier mount 722 may include an electronic drive 730 (e.g., a motor and drive member) that enables automatic movement of the shield mount 720 relative to the carrier mount 722. By providing automatic motion control of the shield 714 (e.g., via the system control and work station 134 shown in FIG. 1), the shield 714 can be configured to automatically be positioned based on how the compression arm assembly 104 (shown in FIG. 1) is moved. In other examples, the technologist can use the electronic drive 730 to position the shield 714 as required or desired.

With either manual shield 714 movement or automatic shield 714 movement, the shield mount 720 and/or the carrier mount 722 may include one or more sensors 732 to determine a position of the shield 714 on the imaging system. In examples, the sensors 732 can provide the position of the shield 714 and, based on the position, indicate to the technologist a direction or a location to move the shield 714 towards. In other examples, the sensors 732 may be used to determine movement direction of the electronic drive 730.

In the example, the sides of the shield 714 may include a pair of wings 734. The wings 734 may be manually pivotable so that each can be aligned in the plane of the shield 714 or in an angled position relative thereto. In an aspect, the wing 734 can be positioned substantially orthogonal to the plane of the shield 714. When the wing 734 is aligned in the plane of the shield 714, the wing 734 may at least partially extend within the carrier mount 722 so that the angular range of motion of the shield 714 is not inhibited. The wings 734 increase a surface area of the shield 714 so as to increase patient comfort, while also providing returns at the side of the shield 714 so as to increase patient support and comfort.

The wings 734 also further restrict the patient from interfering with the x-ray beams during imaging. In aspects, the wings 734 may be removable from the shield 714 as required or desired.

The shield 714 may also include a frame 736 that supports a substantially transparent window member 738. In an aspect, the frame 736 fully extends around the perimeter of the transparent window member 738. In other aspects, the frame 736 only partially extends around the perimeter of the transparent window member 738. In still other aspects, the shield 714 itself may be formed from a substantially transparent material. By allowing the patient to see through the shield 714 patient comfort and calmness are increased. Additionally, the visibility for the technologist is increased.

EXAMPLES

Illustrative examples of the systems and methods described herein are provided below. An embodiment of the system or method described herein may include any one or more, and any combination of, the clauses described below.

Clause 1. An imaging system for imaging a patient's breast including:
a gantry;
a compression arm assembly rotatably coupled to the gantry, the compression arm assembly including a support arm supporting a compression paddle, a platform, and an x-ray receptor disposed below the platform;
an x-ray tube head rotatably coupled to the gantry and independently rotatable relative to the compression arm assembly, the x-ray tube head including an x-ray source that is moveable along a first plane via the x-ray tube head; and
a patient shield system disposed at least partially between the compression paddle and the x-ray source, the patient shield system including:
an arm removably coupled to the support arm;
a carrier slidably coupled to the arm;
a shield; and
a bracket coupling the shield to the carrier, wherein the bracket includes a shield mount coupled to the shield and a carrier mount coupled to the carrier, the shield mount engaged with the carrier mount to allow the shield to be slidingly moved relative to the carrier, and wherein the bracket defines a path of travel for the shield that is in a second plane parallel to the first plane, the path of travel having an arcuate shape.

Clause 2. The imaging system of any one of the clauses herein, wherein the shield includes a flat plate.

Clause 3. The imaging system of any one of the clauses herein, wherein an angular displacement of the shield along the path of travel is at least 60°.

Clause 4. The imaging system of any one of the clauses herein, wherein the carrier mount includes a radiolucent plate secured to the carrier.

Clause 5. The imaging system of any one of the clauses herein, wherein the carrier mount includes a support configured to engage the shield mount and a pair of legs extending from the support and configured to couple to the carrier, and an opening is defined by the support, the pair of legs, and the carrier, the opening shaped and sized to allow x-rays to pass through the patient shield system.

Clause 6. An imaging system for imaging a patient's breast including:

a gantry;

a compression arm assembly rotatably coupled to the gantry, the compression arm assembly including a support arm supporting a compression paddle, a platform, and an x-ray receptor disposed below the platform;

an x-ray tube head rotatably coupled to the gantry and independently rotatable relative to the compression arm assembly around a rotation axis, the x-ray tube head including an x-ray source that is rotatable along a first plane via the x-ray tube head; and a patient shield system disposed at least partially between the compression paddle and the x-ray source, the patient shield system including:

an arm removably coupled to the support arm and defining a longitudinal axis;

a carrier slidably coupled to the arm;

a shield; and a bracket coupling the shield to the carrier, wherein the bracket is configured to allow the shield to move along a transverse plane orthogonal to the longitudinal axis, and wherein a path of travel for the shield along the transverse plane has an arcuate shape.

Clause 7. The imaging system of any one of the clauses herein, wherein a 0° tube head angle is defined as the x-ray tube head being orthogonal to the platform, and wherein the shield is movable along the path of travel between at least ±30° relative to the 0° tube head angle.

Clause 8. The imaging system of any one of the clauses herein, wherein the shield has a first edge and an opposite second edge, and wherein when the shield is moved in a direction towards the first edge, the first edge is positionable past 30°, and when the shield is moved in a direction towards the second edge, the second edge is positionable past –30°.

Clause 9. The imaging system of any one of the clauses herein, wherein the bracket further includes a locking mechanism to secure a position of the shield relative to the carrier.

Clause 10. The imaging system of any one of the clauses herein, wherein the arcuate shape is defined around the rotational axis.

Clause 11. A method of imaging a patient's breast includes:

positioning a compression arm assembly in a first imaging position, the compression arm assembly including a support arm supporting a compression paddle, a platform, and an x-ray receptor disposed below the platform;

immobilizing the patient's breast between the compression paddle and the platform;

positioning a shield at least partially between the patient and an x-ray field of an x-ray source of an x-ray tube head, the shield being coupled to the support arm by at least an arm and a carrier, wherein the shield is movable relative to the support arm linearly along the arm via the carrier and transversely along a plane orthogonal to the arm via a bracket, and wherein a path of travel of the shield is arcuate in shape along the transverse plane;

acquiring one or more first x-ray images in at least one first imagining mode, wherein the at least one first imaging mode is at tube head angles less than or equal to ±7° relative to a 0° tube head angle; and acquiring one or more second x-ray images in a second imaging mode, wherein the second imaging mode is at tube head angles greater than ±7° relative to the 0° tube head angle, and wherein the shield is positioned relative to the x-ray field of the second imaging mode.

Clause 12. The method of any one of the clauses herein, further including locking a position of the shield relative to the compression arm assembly.

Clause 13. The method of any one of the clauses herein, wherein the at least one first imaging mode includes tomosynthesis imaging.

Clause 14. The method of any one of the clauses herein, wherein the at least one first imaging mode includes mammography imaging.

Clause 15. The method of any one of the clauses herein, wherein the at least one first imaging mode includes tomosynthesis and mammography imaging.

Clause 16. The method of any one of the clauses herein, wherein the second imaging mode is mode is enhanced tomosynthesis.

Clause 17. The method of any one of the clauses herein, wherein positioning the compression arm assembly includes positioning the compression arm assembly in an MLO imaging position.

Clause 18. An imaging system for imaging a patient's breast including:

a gantry;

a compression arm assembly rotatably coupled to the gantry, the compression arm assembly including a support arm supporting a compression paddle, a platform, and an x-ray receptor disposed below the platform;

an x-ray tube head rotatably coupled to the gantry and independently rotatable relative to the compression arm assembly, the x-ray tube head including an x-ray source; and a patient shield system disposed at least partially between the compression paddle and the x-ray source, the patient shield system including:

an arm removably coupled to the support arm;

a carrier slidably coupled to the arm;

a shield; and at least one leg supporting the shield on the carrier, wherein a 0° tube head angle is defined as the x-ray source being orthogonal to the support platform, and wherein the at least one leg is positioned on the support arm such that the at least one leg is between a ±8° and ±15° tube head angle.

Clause 19. The imaging system of any one of the clauses herein, wherein when the x-ray source is at a ±8° tube head angle, an image artifact of the at least one leg is not generated during imaging.

Clause 20. The imaging system of any one of the clauses herein, wherein when the x-ray source is at a ±15° tube head angle, an image artifact of the at least one leg is not generated during imaging.

Clause 21. The imaging system of any one of the clauses herein, wherein a cross-sectional profile of the at least one leg is triangular in shape.

Clause 22. The imaging system of any one of the clauses herein, wherein a cross-sectional profile of the at least one leg is circular in shape.

Clause 23. The imaging system of any one of the clauses herein, wherein a cross-sectional profile of the at least one leg is quadrilateral in shape.

Clause 24. The imaging system of any one of the clauses herein, wherein the at least one leg comprises a pair of legs.

Clause 25. A method of imaging a patient's breast including:

immobilizing the patient's breast in a compression arm assembly including a support arm supporting a compression paddle, a platform, and an x-ray receptor disposed below the platform;

positioning a shield at least partially between the patient and an x-ray field of an x-ray tube head, the shield being positioned on one side of a tube head plane with at least one leg supporting the shield and extending across the tube head plane;

acquiring a plurality of x-ray projection images of the patient's breast during tomosynthesis imaging, wherein at least two of the plurality of x-ray projection images include an image artifact from the at least one leg, the at least one leg shaped and sized such that a location of the image artifact within the at least two x-ray projection images do not overlap with one another;

processing the at least two x-ray projection images; and reconstructing one or more tomosynthesis images based on the processed at least two x-ray projection images.

Clause 26. The method of any one of the clauses herein, wherein acquiring the at least two x-ray projection images includes emitting x-ray exposures between a ±8° and ±15° tube head angle.

Clause 27. The method of any one of the clauses herein, wherein processing the at least two x-ray projection images includes identifying a location of the image artifact and segmenting the image artifact with a background value.

Clause 28. The method of any one of the clauses herein, wherein identifying the location of the image artifact includes determining a position of two outermost edges of the image artifact.

Clause 29. The method of any one of the clauses herein, further including processing an x-ray projection image with a partial image artifact of the at least one leg, wherein based on the determined position of at least one of the two outermost edges, a fitting curve is generated such that an edge of the partial image artifact is determined from the at least two x-ray projection images having two outermost edges.

Clause 30. The method of any one of the clauses herein, wherein reconstructing the one or more tomosynthesis images is performed using back-projection in a spatial domain or in a frequency domain.

Clause 31. A method of imaging a patient's breast including:

immobilizing the patient's breast in a compression arm assembly including a support arm supporting a compression paddle, a platform, and an x-ray receptor disposed below the platform;

positioning a shield at least partially between the patient and an x-ray field of an x-ray tube head, the shield being positioned on one side of a tube head plane with at least one leg supporting the shield and extending across the tube head plane;

acquiring a plurality of x-ray projection images of the patient's breast during tomosynthesis imaging, wherein at least one of the plurality of x-ray projection images include an image artifact from the at least one leg;

identifying a location of the image artifact in the at least one x-ray projection image;

segmenting the image artifact with a background value; and reconstructing one or more tomosynthesis images based on the segmented at least one x-ray projection image.

Clause 32. The method of any one of the clauses herein, wherein acquiring the at least one x-ray projection image includes emitting x-ray exposures between a ±8° and ±15° tube head angle.

Clause 33. The method of any one of the clauses herein, wherein the at least one x-ray projection image having the image artifact includes at least two x-ray projection images having the image artifact from the at least one leg, the at least one leg shaped and sized such that a location of the image artifact within the at least two x-ray projection images do not overlap with one another.

Clause 34. The method of any one of the clauses herein, wherein identifying the location of the image artifact includes determining a position of two outermost edges of the image artifact.

Clause 35. The method of any one of the clauses herein, further including processing an x-ray projection image with a partial image artifact of the at least one leg, wherein based on the determined position of at least one of the two outermost edges, a fitting curve is generated such that an edge of the partial image artifact is determined from the at least two x-ray projection images having two outermost edges.

This disclosure describes some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art. Any number of the features of the different examples described herein may be combined into one single example and alternate examples having fewer than or more than all of the features herein described are possible. It is to be understood that terminology employed herein is used for the purpose of describing particular examples only and is not intended to be limiting. It must be noted that, as used in this specification, the singular forms "a," "an," and "the" include plural referents unless the context clearly dictates otherwise.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. An imaging system for imaging a patient's breast comprising:

a gantry;

a compression arm assembly rotatably coupled to the gantry, the compression arm assembly comprising a support arm supporting a compression paddle, a platform, and an x-ray receptor disposed below the platform;

an x-ray tube head rotatably coupled to the gantry and independently rotatable relative to the compression arm assembly, the x-ray tube head comprising an x-ray source that is moveable along a first plane via the x-ray tube head; and a patient shield system disposed at least partially between the compression paddle and the x-ray source, the patient shield system comprising:

an arm removably coupled to the support arm;

a carrier slidably coupled to the arm;

a shield; and a bracket coupling the shield to the carrier, wherein the bracket comprises a shield mount coupled to the shield and a carrier mount coupled to the carrier, the shield mount engaged with the carrier mount to allow the shield to be slidingly moved relative to the carrier, and wherein the bracket defines a path of travel for the shield that is in a second plane parallel to the first plane, the path of travel having an arcuate shape.

2. The imaging system of claim 1, wherein the shield comprises a flat plate.

3. The imaging system of claim 1, wherein an angular displacement of the shield along the path of travel is at least 60°.

4. The imaging system of claim 1, wherein the carrier mount comprises a support configured to engage the shield mount and a pair of legs extending from the support and configured to couple to the carrier, and wherein an opening is defined by the support, the pair of legs, and the carrier, the opening shaped and sized to allow x-rays to pass through the patient shield system.

5. The imaging system of claim 1, wherein a 0° tube head angle is defined as the x-ray tube head being orthogonal to the platform, and wherein the shield is movable along the path of travel between at least ±30° relative to the 0° tube head angle.

6. The imaging system of claim 5, wherein the shield has a first edge and an opposite second edge, and wherein when the shield is moved in a direction towards the first edge, the first edge is positionable past 30°, and when the shield is moved in a direction towards the second edge, the second edge is positionable past −30°.

7. The imaging system of claim 1, wherein the bracket further comprises a locking mechanism to secure a position of the shield relative to the carrier.

8. The imaging system of claim 1, wherein the arcuate shape is defined around a rotational axis of the x-ray tube head.

9. An imaging system for imaging a patient's breast comprising:

a gantry;

a compression arm assembly rotatably coupled to the gantry, the compression arm assembly comprising a support arm supporting a compression paddle, a platform, and an x-ray receptor disposed below the platform;

an x-ray tube head rotatably coupled to the gantry and independently rotatable relative to the compression arm assembly, the x-ray tube head comprising an x-ray source; and a patient shield system disposed at least partially between the compression paddle and the x-ray source, the patient shield system comprising:

an arm removably coupled to the support arm;

a carrier slidably coupled to the arm;

a shield; and at least one leg supporting the shield on the carrier, wherein a 0° tube head angle is defined as the x-ray source being orthogonal to the support platform, and wherein the at least one leg is positioned on the support arm such that the at least one leg is between a ±8° and ±15° tube head angle.

10. The imaging system of claim 9, wherein when the x-ray source is at a ±8° tube head angle, an image artifact of the at least one leg is not generated during imaging.

11. The imaging system of claim 9, wherein when the x-ray source is at a ±15° tube head angle, an image artifact of the at least one leg is not generated during imaging.

12. The imaging system of claim 9, wherein a cross-sectional profile of the at least one leg is circular in shape.

13. The imaging system of claim 9, wherein the at least one leg comprises a pair of legs.

14. A method of imaging a patient's breast comprising:

positioning a compression arm assembly in a first imaging position, the compression arm assembly including a support arm supporting a compression paddle, a platform, and an x-ray receptor disposed below the platform;

immobilizing the patient's breast between the compression paddle and the platform;

positioning a shield at least partially between the patient and an x-ray field of an x-ray source of an x-ray tube head, the shield being coupled to the support arm by at least an arm and a carrier, wherein the shield is movable relative to the support arm linearly along the arm via the carrier and transversely along a plane orthogonal to the arm via a bracket, and wherein a path of travel of the shield is arcuate in shape along the transverse plane;

acquiring one or more first x-ray images in at least one first imagining mode, wherein the at least one first imaging mode is at tube head angles less than or equal to ±7° relative to a 0° tube head angle; and acquiring one or more second x-ray images in a second imaging mode, wherein the second imaging mode is at tube head angles greater than ±7° relative to the 0° tube head angle, and wherein the shield is positioned relative to the x-ray field of the second imaging mode.

15. The method of claim 14, further comprising locking a position of the shield relative to the compression arm assembly.

16. The method of claim 14, wherein the at least one first imaging mode includes tomosynthesis imaging.

17. The method of claim 14, wherein the at least one first imaging mode includes mammography imaging.

18. The method of claim 14, wherein the at least one first imaging mode includes tomosynthesis and mammography imaging.

19. The method of claim 14, wherein the second imaging mode is mode is enhanced tomosynthesis.

20. The method of claim 14, wherein positioning the compression arm assembly includes positioning the compression arm assembly in an MLO imaging position.

* * * * *